US006379903B1

(12) United States Patent
Brizzard et al.

(10) Patent No.: US 6,379,903 B1
(45) Date of Patent: Apr. 30, 2002

(54) PURIFICATION OF RECOMBINANT PROTEINS FUSED TO MULTIPLE EPITOPES

(75) Inventors: Billy L. Brizzard, St. Louis; Ron Hernan, Ballwin, both of MO (US)

(73) Assignee: Sigma-Aldrich Co., Highland, IL (US)

( * ) Notice: Subject to any disclaimer, the term of this patent is extended or adjusted under 35 U.S.C. 154(b) by 0 days.

(21) Appl. No.: 09/415,000

(22) Filed: Oct. 8, 1999

(51) Int. Cl.[7] .................. G01N 33/53; C12N 15/63; C07H 21/02
(52) U.S. Cl. .................. 435/7.1; 435/6; 435/91.1; 435/91.2; 435/320.1; 260/112; 260/112.5; 260/113; 536/23.1; 536/24.2
(58) Field of Search .................. 435/6, 91.1, 91.2, 435/7.1, 320.1; 260/113, 112, 112.5; 536/23.1, 24.2

(56) References Cited

U.S. PATENT DOCUMENTS

| 4,366,246 A | 12/1982 | Riggs .................. 435/68 |
| 4,468,464 A | 8/1984 | Cohen et al. .................. 435/317 |
| 4,503,142 A | 3/1985 | Berman et al. .................. 435/6 |
| 4,532,207 A | 7/1985 | Brewer et al. .................. 435/68 |
| 4,559,302 A | 12/1985 | Ingolia .................. 435/172.3 |
| 4,563,424 A | 1/1986 | Riggs .................. 435/71 |
| 4,569,794 A | 2/1986 | Smith et al. |
| 4,571,421 A | 2/1986 | Itakura .................. 536/27 |
| 4,650,756 A | 3/1987 | Old et al. .................. 435/68 |
| 4,681,848 A | 7/1987 | Tsukamoto et al. .................. 435/240 |
| 4,703,004 A | 10/1987 | Hopp et al. .................. 435/68 |
| 4,782,137 A | 11/1988 | Hopp et al. .................. 530/328 |
| 4,810,632 A | 3/1989 | McMillan .................. 435/7 |
| 4,851,341 A | 7/1989 | Hopp et al. .................. 435/68 |
| 4,978,621 A | 12/1990 | Ardeshir et al. .................. 435/243 |
| 5,011,912 A | 4/1991 | Hopp et al. .................. 530/387 |
| 5,124,251 A | 6/1992 | Lanier et al. .................. 435/7.21 |
| 5,185,438 A | 2/1993 | Lemischka .................. 536/23.2 |
| 5,242,822 A | 9/1993 | Marullo et al. .................. 435/252.3 |
| 5,270,458 A | 12/1993 | Lemischka .................. 536/23.5 |
| 5,336,597 A | 8/1994 | McMillan .................. 435/7.2 |
| 5,731,425 A | 3/1998 | Brizzard et al. .................. 536/23.1 |
| 5,935,824 A | 8/1999 | Sgarlato .................. 435/69.7 |
| 5,945,292 A | 8/1999 | Brizzard et al. .................. 435/7.21 |

FOREIGN PATENT DOCUMENTS

| EP | 0 035 384 | 9/1981 |
| EP | 0 150 126 | 7/1985 |
| WO | WO 97/44469 | 11/1997 |
| WO | WO 00/68398 | 11/2000 |

OTHER PUBLICATIONS

Craven, Rachel A., et al., "Vectors for the expression of tagged proteins in *Schizosaccharomyces pombe*", Gene, vol. 221, No. 1, Oct. 9, 1998, pp. 59–68.

Forsburg, Susan L., et al., "General purpose tagging vectors for fission yeast", Gene, vol. 191, No. 2, Jun. 3, 1997, pp. 191–195.

Hernan, Ron, et al., "Multiple Epitope Tagging of Expressed Proteins for Enhanced Detection", BioTechniques, vol., 28, No. 4, Apr. 2000, pp. 789–793.

International Search Report for Application No. PCT/US 00/25693 filed Sep. 20, 2000.

Alzari et al., "Three–Dimensional Structure of Antibodies", Annu. Rev. Immunol., vol. 6, pp. 555–580 (1988).

Bianca et al., "Use the Flag® Epitope to Examine Expression and Function of a Synthetic Gene Encoding a Cell Surface Protein in Mammalian Cells", Mol. Biol. Cell, vol. 4 (Suppl), #1121, (1993) Abstract.

Borjigin, J., et al., "Insertional Mutagenesis as a Probe of Rhodopsin's Topography, Stability, and Activity", J. Biol. Chem., vol. 269, No. 20, pp. 14715–14722 (1994).

Brizzard, B., et al., "Epitope Tagging of Recombinant Proteins", Current Protocols in Neuroscience, p. 5.8.1–5.8.11.

Chang, Jui–Yoa, "Thrombin Specificity/Requirement for apolar amino acids adjacent to the thombin cleavage sites of polypeptide substrate", Eur. J. Biochem., vol. 151, p. 217–224 (1985).

Dan, et al., "Hamster UDP–N–Acetylglucosamine:Dolichol–P N–Acetylglucosamine–1–P Transferase Has Multiple Transmembrane Spans and a Critical Cytosolic Loop", J. Bio. Chem., vol. 271, No. 48, pp. 30717–30724 (1996).

Davies et al., "Antibody–Antigen Complexes", Annu. Rev. Biochem., vol. 59, pp. 439–473 (1990).

Fan, F., et al., "Enzymatic Characterization of FliI", J. Biol. Chem, vol. 271, No. 50, pp. 31981–31988 (1996).

Goodman and Gilman, Pharm. Basis of Therapeutics, 4th Edition, pp. 948–953 (1970).

Hopp, T., et al., "A short polypeptide marker sequence useful for recombinant protein identification and purification", Bio Technology, vol. 6, pp. 1204–1210 (1988).

(List continued on next page.)

*Primary Examiner*—Carla J. Myers
*Assistant Examiner*—Janell E. Taylor
(74) *Attorney, Agent, or Firm*—Senniger, Powers, Leavitt & Roedel

(57) ABSTRACT

The present invention provides novel identification polypeptides containing multiple copies of an antigenic domain joined in tandem to provide increased sensitivity for the detection and purification of target peptides, a cleavable linking sequence and optionally a spacer domain. Further provided are hybrid polypeptide molecules composed of an identification polypeptide and a target peptide which are produced by recombinant DNA technology and purified using affinity chromatography using one or more ligands. Accordingly, also provided are DNA expression vectors containing DNA encoding for identification polypeptides and methods for using such identification polypeptides for the purification of target peptides. Also provided are methods of constructing DNA vectors encoding the novel identification polypeptides and DNA expression vectors encoding the identification polypeptides linked to a target peptide.

43 Claims, 5 Drawing Sheets-

OTHER PUBLICATIONS

Hopp, T., et al., "Prediction of protein antigenic determinants from amino acid sequences", Proc. Natl. Acad. Sci., vol. 78, No. 6, pp. 3824–3828 (1981).
Hosfield, T., et al., "Influence of the Amino Acid Residue Downstream of (Asp)$_4$Lys on Enterokinase Cleavage of a Fusion Protein", Anal. Biochem vol. 269, pp. 10–6 (1999).
Iliades, P., et al, "Single–Chain Fv of Anti–idiotype 11–1G10 Aantibody Interacts with Antibody NC41 Single–Chain Fv with a Higher Affinity than the Affinity for the Interaction of the Parent Fab Fragments", J. Protein Chem., vol. 17, No. 3, pp. 245–254 (1998).
Kozak, M., "Point mutations close to the AUG initiator codon affect the efficiency of translation of rat prepoinsulin in vivo", Nature, vol. 308, pp. 241–246 (1984).
Kriegler, Michael, "Gene Transfer and Expression/A Laboratory Manual", W.H. Freeman and Company, New York, pp. 23–102, (1990).
Lauritzen, et al., "BPTI and N–Teriminal Extended Analogues Generated by Factor X$_2$ Cleavage and Cathespin C Trimming of a Fusion Protein Expressed in *Escherichia coli*", Prot. Expr. and Purif., vol. 2, pp. 372–378 (1991).
Matsushima, M., et al., "Purification and Further Characterization of Enteropeptidase from Porcine Duodenum", J. Biochem (Tokyo), vol. 125, pp. 947–951 (1999).
Matthey, B., et al., "A new series of pET–derived vectors for high efficiency expression of Pseudomonas exotoxin–based fusion proteins", Gene, vol. 229, pp. 145–153 (1999).
Nagai, K., et al., "Generation of β–globin by sequence–specific proteolysis of a hybrid protein produced in *Escherichia coli*", Nature, vol. 309, No. 28, pp. 810–812 (1984).
Novotny, et al., Antigenic determinants in proteins coincide with surface regions accessible to large probes (antibody domains), Proc. Nat. Acad. Sci., vol. 83, pp. 226–230 (1986).
Okayama, H., et al., "A cDNA Cloning Vector That Permits Expression of cDNA Inserts in Mammalian Cells", Mol. Cell. Biol., vol. 3, No. 2, pp. 280–289 (1983).
Orkin, et al., "Report & Recommendation of the Panel to Assess the NIH Investment in Research on Gene Therapy", (1995).
Overholt, S., et al., "Head and Neck Squamous Cell Growth Suppression Usin Adenovirus–p53–FLAG: A Potential Marker for Gene Therapy Trials", Clin. Cancer. Res., vol. 3, pp. 185–191 (1997).
Padmanabhan, et. al., "Magnetic Affinity Cell Sorting to Isolate Transiently Transfected Cells, Multidrug–Resistant Cells, Somatic Cell Hybrids, and Virally Infected Cells", Methods in Enzymology, vol. 218, pp. 637–651 (1993).
Slootstra, J., et al., "Screening of a Small Set of Random Peptides: A New Strategy to Identify Synthetic Peptides that Mimic Eptitopes", J. Mol. Recognit., vol. 10, pp. 217–224 (1997).
Southern et al., "Transformation of Mammalian Cells to Antibiotic Resistance with a Bacterial Gene Under Control of the SV40 Early Region Promoter", J. Mol. Appl Gen., vol. 1, pp. 327–341 (1982).
Velander, et al., "Process Implications for Metal–Dependent Immunoaffinity Interactions", Biotechnology Progress, vol. 5, No. 3, pp. 119–125 (1989).
Wigler, et al., "Transfer of Purified Hepres Virus Thymidine Kinase Gene to Cultured Mouse Cells", Cell, vol. 11, pp. 223–232 (1977).

Akiba, H., et al., "CD27, a Member of the Tumor Necrosis Factor Receptor Superfamily, Activates NF–kB and Stress–activated Protein Kinase/c–Jun N–terminal Kinase via TRAF2, TRAF5, and NF–kB–inducing Kinase", J. Biol. Chem., vol. 273, No. 21, pp. 13353–13358 (1998).
Benjamin, D., et al., "The Antigenic Structure of Proteins: A Reappraisal", Annu. Rev. Immunol., vol. 2, p. 67–101 (1984).
Brizzard, B., et al., "Immunoaffinity Purification of FLAG® Epitope–Tagged Bacterial Alkaline Phosphatase Using a Novel Monoclonal Antibody and Peptide Elution", Bio Techniques, vol. 16, No. 4, pp. 730–735 (1994).
Favre, L., et al., "Influence of Calcium on Angiotensin II–Antibody Reaction", Immunochemistry, vol. 10, pp. 43–49 (1973).
Frankel, M., et al., "Hydrogen Exchange Studies of a Ca++ Dependent Sheep HSA–ANTI System", Fed. Proceed, vol. 36, p. 1286 (1977).
Invitrogen Internet Search, "Anti–Xpress™ Antibody", Catalog No. R910–26, Version F, http://www.invitrogen.com., pp. 1–9 (1999).
Invitrogen Internet Search, "Differentiate Nearly Identical Recombinant Proteins Using the EpiTag™ System", http://www.invitrogen.com/exprressions/297–7.html, pp. 1–2 (1999).
Invitrogen internet Search, "Index for the Epitag™ Vector Collection", http://www.invitrogen.com/catalog project/cat mamepitag.html, pp. 1–13 (1999).
Invitrogen Internet Search, "Monoclonal Antibody Products", http://www.invitrogen.com/catalog project/cat mab.html, pp. 1–8 (1999).
Invitrogen Internet Search, "pcDNA6/His A, B, and C", Catalog No. V222–20, Version A, http://www.invitrogen.com, pp. 1–19 (1999).
Invitrogen Internet Search, "pcDNA4/His A, B, and C", Catalog No. V862–20, Verison A, http://www.in- vitrogen.com, pp. 1–21 (1999).
Invitrogen Internet Search, "pcDNA4/HisMax A, B, and C", Catalog No. V864–20, Version A, http://www.invitrogen.com, pp. 1–22 (1999).
Invitrogen Internet Search, "The Convenience of pcDNA3.1(–)/Myc–His", http://www.invitrogen.com/expressions/1096–3.html, p. 1 (1999).
Invitrogen Internet Search, "Three Versatile, High–Level Mammalian Expression Vectors", http://www.invitrogen.com/expressions/mamvec.html, pp. 1–2 (1999).
Itamura, S., et al., "Expression of the gag gene of human T–cell leukemia virus type I in *Escherichia coli* and its diagnostic use", Gene, vol. 38, pp. 57–64 (1985).
Jin, Lei, et al., "High Resolution Functional Analysis of Antibody–Antigen Interactions", J. Mol. Biol., vol. 116, pp. 851–65 (1992).
Knappik, A., et al., "An improved Affinity Tag Based on the FLAG® Peptide for the Detection and Purification of Recombinant Antibody Fragments", BioTechniques, vol. 17, No. 4, pp. 754–761 (1994).
Lefebvre, P., et al., "Binding of Retinoic Acid Receptor Heterodimers to DNA", J. Biol. Chem., vol. 273, No. 20, pp. 12288–12295 (1998).
Lehninger, A.L., Principles of Biochemistry, pp. 149–150 (1970).
Livingston, et al., "Immunoaffinity Chromatography of Proteins", Methods in Enzymol., vol. 70, pp. 723–731 (1980).

Maurer, P., et al., "Antigenicity of Polypeptides (PolyαAmino Acids): Calcium–Dependent and Independent Antibodies", J. Immunol., vol. 105, No. 3, pp. 567–573 (1970).

Maurer P., et al., "Proteins and Polypeptides as Antigens", Methods in Enzymol, vol. 70, pp. 49–59 (1980).

Miceli, R., et al., "Two–stage selection of sequence from a random phage display library delineates both core residues and permitted structural range within an epitope", Journal of Immunological Methods, vol. 167, pp. 279–287 (1994).

Nilsson, J., et al., "Multiple Affinity Domains for the Detection, Purification and Immobilization of Recombinant Proteins", Journal of Molecular Recognition, vol. 9, pp. 585–594 (1996).

Prickett, K., et al., "A Calcium–Dependent Antibody for Identification and Purification of Recombinant Proteins", BioTechniques, vol. 7, pp. 580–589 (1989).

Reed, "Preparation of Product–Specific Antisera by Gene Fusion: Antibodies Specific for the Product of the Yeast Cell–Division–Cycle Gene CDC28", Gene, vol. 20, pp. 255–265 (1982).

Ross–MacDonald, P., et al., "A multipurpose transposon system for analyzing protein production, localization, and function in *Saccharomyces cerevisiae*", Proc. Natl. Acad. Sci. USA, vol. 94, pp. 190–195 (1997).

Sassanfeld, H., et al., "A Polypeptide Fusion Designed for the Purification of Recombinant Proteins", Bio/Technology, p. 76–81 (1984).

Sheffield, P., et al., "Overcoming Expression and Purification Problems of RhoGDI Using a Family of "Parallel" Expression Vectors", Protein Expression and Purification, vol. 15, pp. 34–39 (1999).

Shuman H., et al., "Labeling of Proteins with β–Galactosidase by Gene Fusion", J. Biol. Chem. vol. 255, No. 1, pp. 168–174 (1980).

Slootstra, J., et al., "Identification of new tag sequences with differential and selective recognition properties for the anti–FLAG monoclonal antibodies M1, M2 amd M5", Molecular Diversity, vol. 2, pp. 156–164 (1996).

Smith, J., et al., "Chemical Synthesis and Cloning of a Poly(arginine)–Coding Gene Fragment Designed to Aid Polypeptide Purification", Gene, vol. 32, pp. 321–327 (1984).

Tucker, J., "Purification of a rat neurotensin receptor expressed in *Escherichia coli*", Biohcem. J., vol. 317, pp. 891–899 (1996).

FIG. 1A

```
                                                                                          Hind III
AAG GAT GAC GAT GAC  ATG GAC TAC AAA GAC CAT GAC GGT GAT TAT AAA GAT CAT GAT ATC GAT TAC
TAC CTA CTG CTA CTG  TAC CTG ATG TTT CTG GTA CTG CCA CTA ATA TTT CTA GTA CTA TAG CTA ATG
Lys Asp Asp Asp Asp  Met Asp Tyr Lys Asp His Asp Gly Asp Tyr Lys Asp His Asp Ile Asp Tyr Hind III              Pst I         Sal I         Xba I              BamH I    Sma I
    AAG CTT GCA TGC GGT CTG CAG GTC GAC TCT AGA TCT AGA GGA TCC CGG G
    TTC GAA CGT ACG CCA GAC GTC CAG AGA TCT AGA TCT CCT AGG GCC C
    Lys Leu Ala Cys Gly Leu Gln Val Asp Ser Arg Ser Arg Gly Ser Arg
```

Western Blot

PURIFICATION OF RECOMBINANT PROTEINS FUSED TO MULTIPLE EPITOPES

FIELD OF THE INVENTION

The present invention relates to protein tags and methods of protein purification using various recombinant DNA techniques. More particularly, the invention is directed to novel identification polypeptides and DNA vectors encoding novel identification polypeptides containing multiple antigenic domains joined in tandem. Also provided are methods for using such identification polypeptides for the purification of target peptides and methods of constructing DNA vectors encoding the novel identification polypeptides and DNA expression vectors encoding the identification polypeptides linked to a target peptide.

BACKGROUND OF THE INVENTION

Proteinaceous molecules such as enzymes, hormones, storage proteins, binding proteins, transport proteins and signal transduction proteins may be produced and purified using various recombinant DNA techniques. For instance, DNA fragments coding for a selected protein, together with appropriate DNA sequences for a promoter and ribosome binding site are ligated to a plasmid vector. The plasmid is inserted within a host prokaryotic or eukaryotic cell. Transformed host cells are identified, isolated and then cultivated to cause expression of the proteinaceous molecules. One method used to purify hybrid polypeptides is the polyarginine system in which a hybrid polypeptide is selectively purified on a cation exchange resin. See Sassenfeld, H. M. and Brewer, S. J. *BioTechnology*, 2:76 (1984); U.S. Pat. No. 4,532,207. Sassenfeld and Brewer reported a carboxy-terminal extension of five arginine residues fused to a target protein. This basic polyarginine extension allowed the purification of the hybrid polypeptide on a SP-Sephadex resin. An analogous protein expression and purification system employs a polyhistidine tract or tag at either the amino- or carboxy-terminus of the hybrid polypeptide. The fusion protein is purified by chromatography on a $Ni^{2+}$ metal affinity resin. See Porath, J., *Protein Expression and Purification*, 3:7995 (1992).

Additionally, various affinity purification protocols are currently employed to facilitate the isolation of fusion proteins. Affinity chromatography is based on the capacity of proteins to bind specifically and noncovalently with a ligand. Used alone, it can isolate proteins from very complex mixtures with not only a greater degree of purification than possible by sequential ion-exchange and gel column chromatography, but also without significant loss of activity. Typically, a ligand capable of binding with high specificity to an affinity matrix is chosen as the fusion partner. For example, p-aminophenyl-β-D-thiogalactosidyl-succinyldiaminohexyl-Sephar ose selectively binds to β-galactosidase allowing the purification of β-gal fusion proteins. See Germino et al., *Proc. Natl. Acad. Sci. USA* 80:6848 (1983). Other expression systems which permit the affinity purification of fusion proteins include fusion proteins made with glutathione-S-transferase, which are selectively recovered on glutathione-agarose. See Smith, D. B. and Johnson, K. S. *Gene* 67:31 (1988). IgG-Sepharose can be used to affinity purify fusion proteins containing staphylococcal protein A. See Uhlen, M. et al. *Gene* 23:369 (1983). The maltose-binding protein domain from the malE gene of *E. coli* has been used as a fusion partner and allows the affinity purification of the fusion protein on amylose resins.

Another method used to detect and isolate proteins is by use of an epitope tag. Epitope tagging utilizes antibodies against guest peptides to study protein localization at the cellular level and subcellular levels. See Kolodziej, P. A. and Young, R. A., *Methods Enzymol.*, 194:508–519 (1991). Using recombinant DNA technology, a sequence of nucleotides encoding the epitope is inserted into the coding region of the cloned gene, and the hybrid gene is introduced into a cell by a method such as transformation. When the hybrid gene is expressed the result is a chimeric protein containing the epitope as a guest peptide. If the epitope is exposed on the surface of the protein, it is available for recognition by the epitope-specific antibody, allowing the investigator to observe the protein within the cell using immunofluorescence or other immunolocalization techniques. Further, fusion proteins labeled with such epitope tags are frequently used for purifying proteins utilizing affinity purification techniques.

Thus, epitope tagging has become a powerful tool for the detection and purification of expressed proteins. See Kolodziej, P. A. and Young, R. A., *Methods Enzymol.*, 194:508–519 (1991). Many types of tags have been used, with c-myc and FLAG® tags being two of the most popular epitopes used. See Evan et al., *Mol Cell Biol.* 5:3610–3616 (1985). Generally, these epitopes are fused to the amino or carboxy-terminus of the expressed protein making them more accessible to the antibody for detection and less likely to cause severe structural or functional perturbations.

Fusion proteins having the FLAG® octapeptide Asp-Tyr-Lys-Asp-Asp-Asp-Asp-Lys (SEQ ID NO:1) at the amino-terminus can be affinity purified on an immuno-affinity resin containing an antibody specific for the octapeptide, See Hopp, T. P., et al. *Biotechnology,* 6:1204 (1988); Prickett, K. S., et al., *BioTechniques,* 7:580 (1989); and U.S. Pat. No. 4,851,341. The FLAG® epitope tag has been effectively used to detect and purify protein in mammalian and bacterial systems. The original FLAG® sequence is recognized by two antibodies, M1, M2, and a FLAG® sequence with an initiator methionine attached is recognized by a third antibody, M5. The last five amino acids of the FLAG® sequence is a recognition site for the protease enterokinase, thus, allowing for removal of the FLAG® epitope. The FLAG® epitope has been used in various expression systems for detection and purification of heterologous proteins e.g., in *E. coli* (Brizzard et al., *BioTechniques,* 16:730–735 (1994)), *Saccharomyces cerevisiae* (Lee et al., *Nature,* 372:739–746 (1994); Prickett et al., *BioTechniques,* 7:580–589 (1989)), Drosophila (Xu et al., *Development,* 117:1223–1237 (1993)), Baculovirus (Dent et al., *Mol.Cell Biol,* 15:4125–4135 (1995); Ritchie et al., *Biochem Journal,* 338:305–10 (1999)), and mammalian systems (Overholt et al., *Clin. Cancer Res.,* 3:185–191 (1997); Schulte am Esch et al., *Biochemistry,* 38:2248–2258 (1999)). However, in many mammalian expression systems, protein expression levels are low and effective detection of expressed foreign proteins using established methods can be difficult.

There is therefore a need for an epitope tag and expression system employing such epitope tags which would allow for increased sensitivity and detection of recombinant proteins.

SUMMARY OF THE INVENTION

The present invention addresses one or more of the foregoing problems by providing methods and vehicles which can be used to produce high yields of recombinant proteins. Accordingly, among the several objects of the present invention may be noted the provision of a novel identification polypeptide, a hybrid molecule composed of a target peptide fused to the novel identification polypeptide and recombinant DNA vectors encoding the same. Also provided are methods for the purification of the target peptide wherein a single ligand or multiple ligands, preferably antibodies may be employed to isolate and purify substantially all protein molecules expressed by transformed host cells, whether antigenic or not. A further object of the present invention is to provide processes which can be used to highly purify any protein molecule produced by recombinant DNA methods, including those that are not susceptible to affinity chromatography procedures.

Briefly, therefore, the present invention is directed to an identification polypeptide comprising multiple copies of an antigenic domain joined together in tandem. The identification polypeptide may contain a linking sequence containing a cleavable site located adjacent to the target peptide wherein the cleavable site is not located in or interposed between the individual antigenic domains. Each antigenic domain is capable of eliciting an antigenic response and can be bound by a ligand, preferably an antibody. Further, each antigenic domain is comprised of a combination of at least two, preferably three or more different amino acids.

Also provided are fusion proteins of the present invention comprising the novel identification polypeptide fused to a target peptide. The identification polypeptide contains a linking sequence which is characterized by being cleavable at a specific amino acid residue adjacent to the target peptide by use of a sequence specific proteolytic agent. Such cleavable site is located adjacent to either the carboxy-terminus or amino-terminus of the target peptide, preferably located immediately adjacent to the amino-terminus of the target peptide. Ideally, the amino acid sequence of the cleavable site is unique, thus minimizing the possibility that the proteolytic agent will cleave the target peptide. In a preferred embodiment, the cleavable site comprises amino acids specific for enterokinase, thrombin or a Factor Xa.

In accordance with this particular construct of the fusion protein, the target peptide may be isolated by affinity chromatography techniques. Thus, it is an object of the invention to provide methods for the purification of the target peptide. This is accomplished by constructing an affinity column with immobilized ligands specific for the antigenic domains of the identification polypeptide thereby binding the fusion protein. It will be appreciated that by virtue of the present invention, a singular antibody or multiple antibodies may be used to bind to the individual antigenic domains comprising the multiple antigenic domains of the identification polypeptide. Then the bound fusion protein can be liberated from the column and the identification polypeptide cleaved with an appropriate proteolytic agent, thus releasing a purified target peptide. In a preferred embodiment, the proteolytic agent used to cleave the target peptide from the identification polypeptide is selected from the group consisting of enterokinase, thrombin and Factor Xa.

A further object of the present invention is to provide a recombinant cloning vector containing DNA encoding for the identification polypeptide. The vector encoding for the identification polypeptide also includes DNA sequences coding for a multiple cloning site comprised of multiple restriction enzyme sites which may be located between the antigenic domains or on either side of the antigenic domains which will enable one skilled in the art to insert any number of DNA sequences encoding for any desired protein. This DNA sequence may be inserted within a cloning vector such as a plasmid, by use of appropriate restriction endonucleases and ligases. The recombinant plasmid is employed to transform compatible prokaryotic or eukaryotic host cells for replication of the plasmid and expression of the hybrid affinity domain/protein molecule. Ideally, the plasmid has a phenotypic marker gene for identification and isolation of transformed host cells. In a preferred embodiment, DNA sequences encoding for a secreted signal peptide will be joined either to the DNA vector or to the plasmid thus enabling the transformed host cells to be readily identified and separated from cells which do not undergo transformation.

Other objects and features will be in part apparent and in part pointed out hereinafter.

BRIEF DESCRIPTION OF THE DRAWINGS

FIG. 1A is a depiction of a DNA and protein sequence of 3XFLAG-CMV-7 multiple cloning site and FLAG sequences.

ABBREVIATION AND DEFINITIONS

Figure 1B:
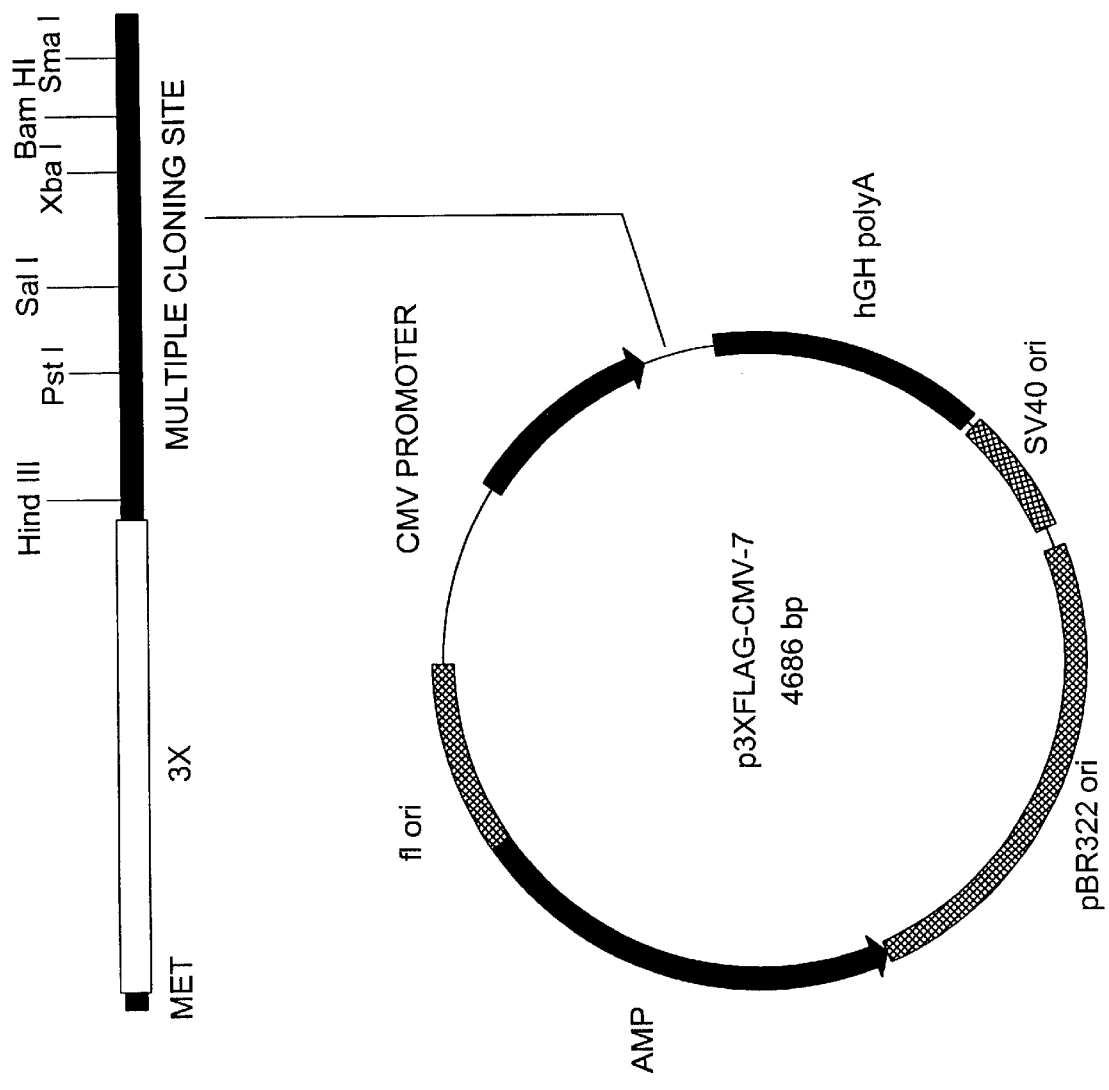
FIG. 1B is a plasmid map of the p3XFLAG-CMV-7 showing the CMV promoter, human growth hormone transcription termination and polyadenylation site, SV40 origin of replication, Col E1 origin of replication, and β-lactamase gene.

To facilitate understanding of the invention, a number of terms are defined below:

The nucleotide bases are abbreviated herein as follows: A represents adenine; C represents cytosine; G represents guanine; T represents thymine; U represents uracil.

The amino acid residues are abbreviated herein according to their single letters: A represents alanine; R represents arginine; N represents asparagine; D represents aspartic acid; C represents cysteine; Q represents glutamine; E represents glutamic acid; G represents glycine; H represents histidine; I represents isoleucine; L represents leucine; K represents lysine; M represents methionine; F represents phenylalanine; P represents proline; S represents serine; T represents threonine; W represents tryptophan; Y represents tyrosine; V represents valine.

The term "recombinant DNA molecule" as used herein refers to a DNA molecule which is comprised of segments of DNA joined together by means of recombinant DNA technology.

The term "expression vector" as used herein refers to nucleic acid sequences containing a desired coding sequence and appropriate nucleic acid sequences necessary for the expression of the operably linked coding sequence in a particular host organism. Nucleic acid sequences necessary for expression in prokaryotes include a promoter, a ribosome binding site, an initiation codon, a stop codon, optionally an operator sequence and possibly other sequences. Eukaryotic cells utilize promoters, a Kozak sequence and often enhancers and polyadenlyation signals. Prokaryotic cells also utilize a Shine-Dalgarno Ribosome binding site. The present invention includes vectors or plasmids which can be used as vehicles to transform any viable host cell with the recombinant DNA expression vector.

The term "FLAG" as used herein is the registered trademark that refers to the widely used FLAG® epitope tag consisting of the synthetic peptide sequence of DYKD-DDDK as described in U.S. Pat. Nos. 4,703,004, 4,782,137, 4,851,341 and 5,011,912 incorporated herein by reference.

The term "hydrophilic" when used in reference to amino acids refers to those amino acids which have polar and/or charged side chains. Hydrophilic amino acids include lysine, arginine, histidine, aspartate (i.e., aspartic acid), glutamate (i.e., glutamic acid), serine, threonine, cysteine, tyrosine, asparagine and glutamine.

The term "hydrophobic" when used in reference to amino acids refers to those amino acids which have nonpolar side chains. Hydrophobic amino acids include valine, leucine, isoleucine, cysteine and methionine. Three hydrophobic amino acids have aromatic side chains. Accordingly, the term "aromatic" when used in reference to amino acids refers to the three aromatic hydrophobic amino acids phenylalanine, tyrosine and tryptophan.

The term "cleavable site" refers to a defined amino acid sequence that allows cleavage of a protein or peptide containing this sequence by a selective proteolytic agent.

The term "fusion protein" as used herein refers to a hybrid polypeptide which comprises protein domains from at least two different proteins. The target peptide may be located at the amino-terminal portion of the fusion protein or at the carboxy-terminal protein thus forming an "amino-terminal fusion protein" or a "carboxy-terminal fusion protein," respectively.

The term "target peptide" as used herein refers to the peptide whose expression is desired within the hybrid polypeptide. In the hybrid polypeptides of the invention, the target peptide may comprise either the amino- or carboxy-terminal portion of the hybrid polypeptide.

The term "endoprotease" or "endopeptidase" as used herein refers to a protease capable of hydrolyzing interior peptide bonds of a polypeptide, at points other than the terminal bonds (i.e., the peptide bonds of the terminal amino acid).

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

For all the nucleotide and amino acid sequences disclosed herein, it is understood that equivalent nucleotides and amino acids can be substituted into the sequences without affecting the function of the sequences. Such substitutions is within the ability of a person of ordinary skill in the art.

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press as incorporated herein by reference.

DETAILED DESCRIPTION

In accordance with the present invention, provided are identification polypeptides with increased sensitivity for the detection and purification of target peptides which are produced using recombinant DNA technology. Further provided are hybrid polypeptide molecules composed of an identification polypeptide and a target peptide which are produced by recombinant DNA technology and purified using affinity chromatography using one or more ligands. Accordingly, also provided are DNA expression vectors which include segments of DNA encoding for the identification polypeptide and the desired target peptide.

In accordance with the present invention, a target peptide may be composed of any proteinaceous substance that can be expressed in transformed host cells. The increased antigenicity of the identification polypeptide results from the presence of multiple copies of an antigenic domain in tandem. The identification polypeptide also contains a cleavable linking sequence which joins the identification polypeptide to target peptide thus producing a hybrid polypeptide. The DNA cloning vectors may be replicated and the hybrid polypeptide composed of the identification polypeptide and a target peptide is expressed in prokaryotic or eukaryotic cells transformed with the vector. The transformed cells are isolated and then expanded in culture or other means known in the art.

Hybrid polypeptide molecules of the present invention may be purified by affinity chromatography. The hybrid polypeptide molecule comprising the identification polypeptide and target peptide may be purified using an affinity resin which binds to the antigenic domains of the identification polypeptide. Generally, ligands specific to the antigenic domains of the identification polypeptide tag are immobilized on a bead column or other type of matrix. An extract of the host cells made from the culture is applied to the column and then the polypeptides that bind to the column are eluted. Thereafter, the identification polypeptide is cleaved from the target peptide molecule with an appropriate proteolytic agent thereby releasing the target peptide in a highly purified state.

Identification Polypeptide

The identification polypeptide of the present invention is a sequence of amino acid residues flanking the amino or carboxy terminus of a target peptide. In general, the identification polypeptide includes multiple copies of an antigenic domain, where each antigenic domain is capable of binding an antibody, a cleavable linking sequence to join the antigenic domains to the target peptide, and optionally one or more spacers.

To increase the detection sensitivity, the identification polypeptide preferably contains multiple copies of an antigenic domain, i.e., at least two copies of an antigenic domain, preferably at least three copies of an antigenic domain and, in some embodiments, four or more copies of an antigenic domain. The ability of the sequence of multiple antigenic domains to bind to an antibody immobilized, for example, on a column or other matrix enables the isolation and purification of target peptides.

Each antigenic domain of the sequence of multiple antigenic domains preferably comprises no more than about twenty amino acid residues, more preferably no more than about fifteen amino acid residues, even more preferably no more than about ten amino acid residues, and still more preferably no more than about six amino acid residues in total. In addition, each antigenic domain preferably comprises at least two, more preferably at least three different amino acid residues, preferably selected from among hydrophilic and aromatic amino acids. While nonaromatic, hydrophobic amino acid residues need not be excluded from the antigenic domains, it is generally preferred that at least one-half of the amino acid residues constituting the antigenic domains be selected from among hydrophilic and aromatic amino acids, still more preferred that at least one-half of the amino acid residues constituting the antigenic domains be hydrophilic amino acids, and still further preferred that at least three-fourths of the amino acid residues constituting the antigenic domains be hydrophilic amino acid residues. In one preferred embodiment, the amino acid residues constituting the antigenic domains are one half hydrophilic amino acids and one half aromatic amino acids. In another preferred embodiment, the amino acid residues constituting the antigenic domains are selected from hydrophilic amino acids.

In one preferred embodiment of the present invention, each antigenic domain is defined by a series of about six to about ten amino acid residues comprising residues of at least three different amino acids with at least one being selected from the group of aromatic amino acids and at least one being selected from the group of hydrophilic amino acids and with the number of hydrophilic amino acid residues constituting at least 50%, more preferably at least 75% of the total number of amino acid residues defining the antigenic domain. Hydrophilic amino acids are preferred as they are more likely to be exposed on the protein surface thus resulting in increased accessibility to the antibody. See Hopp T. P. and Woods K. R., *Proc. Natl. Acad. Sci.*, 78:3824–3828 (1981). Optionally, this sequence may include one or more non-aromatic, hydrophobic residues.

In another embodiment of the present invention, the amino acids of each antigenic domain may be selected from charged or polar amino acid residues. Jin et al. have shown that the amino acids side chains of arginine, proline, glutamic acid, aspartic acid, phenylalanine and isoleucine play a dominant role in the functional epitope of human growth hormone (hGH). See Jin et al., *J. Mol. Biol.* 116:851–865 (1992) as incorporated herein by reference. Additionally, Jin et al. have shown that binding of the epitope to monoclonal antibodies are dominated by a small number of amino acid side chains in the epitope and are often charged or polar amino acid side chains. See Jin et al, supra. Accordingly, designing the antigenic domain using amino acid residues selected from arginine, proline, glutamic acid, aspartic acid, phenylalanine and isoleucine may increase the surface accessibility of the identification polypeptide. See Benjamin et al., *Annu. Rev. Immunol.* 2:101 (1984); Novotny et al., *Proc. Nat. Acad. Sci.*, 83:226–230 (1986); Alzai et al., *Annu. Rev.Immunol.* 6:555–580 (1988); Davies et al., *Annu. Rev. Biochem.*, 59:439–473 (1990).

The identification polypeptide includes a cleavable linking sequence to link the sequence of antigenic domains to the target peptide. In general, the amino acid residues comprising the linking sequence may comprise any amino acid sequence which would serve to connect the sequence of antigenic domains to the target peptide. Furthermore, the linking sequence contains a cleavage site which comprises a unique amino acid sequence cleavable by use of a sequence-specific proteolytic agent. Once the hybrid polypeptide composed of the identification polypeptide and the target peptide has been purified from the culture extract, the identification polypeptide is preferably cleaved from the target peptide by digestion with a proteolytic agent specific for the amino acids of the cleavage site. Alternatively, the identification polypeptide may be removed from the target peptide by chemical cleavage using methods known to the art.

In general, the cleavable site may be located at the amino or carboxy terminus of the target peptide. Preferably, the cleavable site is immediately adjacent the target peptide to enable separation of the target peptide from the identification polypeptide. This cleavable site preferably does not appear in or interposed between the antigenic domains or if present, the spacer domains of the identification polypeptide. In a preferred embodiment, the cleavable site is located at the amino terminus of the target peptide. If the cleavable site is located at the amino terminus of the target peptide and if there are remaining extraneous amino acids on the target peptide after cleavage with the proteolytic agent, an endopeptidase such as trypsin, clostropain or furin may be utilized to remove these remaining amino acids, thus resulting in a highly purified target peptide.

Digestion with a proteolytic agent may occur while the hybrid polypeptide is still bound to the affinity resin or alternatively, the hybrid polypeptide may be eluted from the affinity resin and then digested with the proteolytic agent in order to further purify the target peptide. The efficiency of the proteolytic agent or the chemical cleavage of the recombinant target peptide is determined by the amino acid sequence of the linking sequence interposed between the sequence of antigenic domains and the target peptide.

Ideally, the amino acid sequence of the cleavage site is unique, thus minimizing the possibility that the proteolytic agent will cleave the target peptide. In a preferred embodiment, the cleavable site comprises amino acids for an enterokinase, thrombin or a Factor Xa cleavage site.

Enterokinase recognizes several sequences: Asp-Lys; Asp-Asp-Lys; Asp-Asp-Asp-Lys (SEQ ID NO:3); and Asp-Asp-Asp-Asp-Lys (SEQ ID NO:3). See Matsushima et al., *J. Biochem* 125:947–51 (1999). The only known natural occurrence of Asp-Asp-Asp-Asp-Lys is in the protein trypsinogen which is a natural substrate for bovine enterokinase and some yeast proteins. As such, by interposing a linking sequence containing the amino acid sequence Asp-Asp-Asp-Asp-Lys (SEQ ID NO:3) as a cleavable site between the sequence of antigenic domains and the amino terminus of the target peptide, the target peptide can be liberated from the identification polypeptide by use of bovine enterokinase with very little likelihood that this enzyme will cleave any portion of the target peptide itself.

Thrombin cleaves on the carboxy-terminal side of arginine in the following sequence: Leu-Val-Pro-Arg-Gly-X (SEQ ID NO:4), where X is a non-acidic amino acid. See Chang *Eur. J. Biochem.,* 151:217 (1985). Factor Xa protease (i.e., the activated form of Factor X) cleaves after the Arg in the following sequences: Ile-Glu-Gly-Arg-X (SEQ ID NO:5), Ile-Asp-Gly-Arg-X (SEQ ID NO:6), and Ala-Glu-Gly-Arg-X (SEQ ID NO:7), where X is any amino acid except proline or arginine. A fusion protein comprising the 31 amino-terminal residues of the cII protein, a Factor Xa cleavage site and human β-globin was shown to be cleaved by Factor Xa and generate authentic β-globin. See Nagai, K. and Thogersen, H. C., *Nature,* 308: 810–812 (1984). A limitation of the Factor Xa-based fusion systems is the fact that Factor Xa has been reported to cleave at arginine residues that are not present within in the Factor Xa recognition sequence. See Nagai et al., *Prot. Expr. and Purif.,* 2:372 (1991).

While less preferred, other unique amino acid sequences for other cleavable sites may also be employed in the linking sequence without departing from the spirit or scope of the present invention. For instance, the linking sequence can be composed in part of a pair of basic amino acids, i.e., Lys, Arg or His. This sequence is cleaved by kallikreins, a glandular enzyme. Also, the linking portion can be in part composed of Arg-Gly, since it is known that the enzyme thrombin will cleave after the Arg if this residue is followed by Gly. Further, it is not required that the antigenic domains and the cleavable site be exclusive of one another. Antibodies may be able to bind to amino acids found in the leavable site such as is the case with the FLAG® monoclonal antibody M2 which recognizes part of the cleavable site Asp-Asp-Asp-Asp-Lys (SEQ ID NO:3) for enterokinase.

While it is generally preferred that each antigenic domain be immediately adjacent to another antigenic domain (i.e., no intervening sequences), the antigenic domains may be separated from one another by a spacer domain. A spacer domain may also be inserted between the multiple copies of the antigenic domain and the linking sequence. The insertion of a spacer domain preferably does not result in the insertion of a second copy of the cleavable site between the antigenic domains of the identification polypeptide. It is preferred that the number of amino acid residues in each spacer domain be minimal, preferably consisting of no more than ten amino acid residues, more preferably, no more than about six amino is acid residues, and still more preferably two or even one amino acid residue(s) in length.

If a spacer domain is employed, it may be designed to impart one or more desired properties to the identification polypeptide. In one embodiment, the amino acid(s) of spacer domain are selected from among hydrophilic amino acids to increase the hydrophilic character of the identification polypeptide. Alternatively, the amino acid(s) of the spacer domain may be selected to impart a desired folding to the identification polypeptide thereby increasing accessability to the antibody; for example, the spacer domain may comprise glycine residues which results in a protein folding conformation which allows for improved accessibility to the antibody. See Dan et al., *J. Bio. Chem.* 271:30717–30724 (1996); Borjigin, J. and Nathans, J., *J. Biol. Chem.* 269:14715–147622 (1994).

It is well known in the art that certain amino acid residues such as histidine have an affinity to bind or chelate immobilized metal ions. Accordingly, designing an identification polypeptide with a metal chelating sequence composed of multiple or alternating histidine residues in the spacer domain or flanking either side of the sequence of antigenic domains would allow the hydrid polypeptide to bind to a metal ion immobilized on a resin or other matrix. In a preferred embodiment, a metal chelating sequence flanking the multiple copies of the antigenic domain or in a spacer domain may comprise at least one histidine residue, at least one glycine residue or a combination of alternating or multiple histidine residues of the formula: —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro, which may be used in affinity purification techniques using a Ni$^{2+}$ binding metal resin. See, for example, U.S. Pat. Nos. 4,569,794, 5,310,663, 5,284,933 and 5,594,115 which are incorporated herein by reference. Preferably, the amino acids of the spacer domain do not include a second copy of the cleavable site as described herein. Once the hybrid polypeptide is bound to the metal resin, the hybrid polypeptide can be released by protonation of its associated metal ion-binding ligand. Dissociation is achieved by lowering the pH of the surrounding buffer medium, a common method known in the art for eluting bound proteins.

In one embodiment of the present invention, the identification polypeptide comprises multiple copies of an antigenic domain generally corresponding to the FLAG® peptide sequence joined to a linking sequence containing a single enterokinase cleavage site. Such identification polypeptide generally corresponds to the sequence:

$$X^{20}-(X^1-Y-K-X^2-X^3-D-X^4)_n-X^5-(X^1-Y-K-X^7-X^8-D-X^9-K)-X^{21}$$

where:

D, Y and K are their representative amino acids;

$X^{20}$ and $X^{21}$ are independently a hydrogen or a bond;

each $X^1$ and $X^4$ is independently a bond or at least one amino acid residue, if other than a bond, preferably at least one amino acid residue selected from the group consisting of aromatic amino acid residues and hydrophilic amino acid residues, more preferably at least one hydrophilic amino acid residue, and still more preferably at least one aspartate residue;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a bond or a spacer domain comprising at least one amino acid, if other than a bond, preferably a histidine residue, a glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Ala, Glu, Ile, Thr, Asp, Asn, Gln, Arg, Cys, and Pro;

$X^9$ is a bond or D; and n is at least 2.

In this embodiment, the amino acid sequence $X^{20}-(X^1-Y-K-X^2-X^3-D-X^4)_n$, represents the multiple copies of antigenic domain —$X^1-Y-K-X^2-X^3-D$— joined in tandem which are joined to a linking sequence ($X^1-Y-K-X^7-X^8-D-X^9-K$). The antigenic domains may be immediately adjacent to each other when $X^4$ is a bond, optionally, $X^4$ may be a spacer domain interposed between the multiple copies of antigenic domains. The linking sequence contains a single enterokinase cleavable site which is represented by the sequence —$X^7-X^8-D-X^9-K$, where $X^7$ and $X^8$ may be an amino acid residue or a bond and $X^9$ is a bond or an aspartate residue. In a preferred embodiment, each $X^7$, $X^8$ and $X^9$ is independently an aspartate residue thus resulting in the enterokinase cleavable site DDDDK which is preferably located immediately adjacent to the amino terminus of the target peptide. The multiple copies of antigenic domains may be immediately adjacent to the linking sequence when $X^5$ is a bond, optionally, $X^5$ may be a spacer domain interposed between the linking sequence and the antigenic domains. When each $X^4$ and $X^5$ is independently a spacer domain, it is preferred that the amino acid residue(s) of each $X^4$ and $X^5$ impart one or more desired properties to the identification polypeptide; for example, the amino acids of the spacer domain may be selected to impart a desired folding to the identification polypeptide thereby increasing accessibility to the antibody. In another preferred embodiment, the amino acids of the spacer domain $X^4$ and $X^5$ may be selected to impart a desired affinity characteristic such as a combination of multiple or alternating histidine residues capable of chelating to an immobilized metal ion on a resin or other matrix. Furthermore, these desired properties may be designed into other areas of the identification polypeptide; for example, the amino acids represented by $X^2$ and $X^3$ may be selected to impart a desired peptide folding or a desired affinity characteristic for use in affinity purification.

In a more preferred embodiment, the identification polypeptide comprises multiple copies of an antigenic domain, a linking sequence containing a single enterokinase cleavage site and generally corresponds to the sequence:

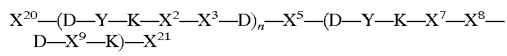

where:

D, Y, K are their representative amino acids;

$X^{20}$ and $X^{21}$ are independently a hydrogen or a bond;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a bond or a spacer domain comprising at least one amino acid, if other than a bond, preferably a histidine residue, a glycine residue or a combination of multiple or alternating histidine residues, said combination comprising His-Gly-His, or —(His-X)$_m$—, wherein m is 1 to G and X is selected from the group consisting of Gly, His, Tyr, Trp, Val, Leu, Ser, Lys, Pe, Met, Ala, Glu, Ile, Thr, Asp, Asn, Gln, Arg, Cys, and Pro;

$X^9$ is a bond or an aspartate residue; and n is at least 2.

In this embodiment, the amino acid sequence $X^{20}$—(D—Y—K—$X^2$—$X^3$—D)$_n$ represents the multiple copies of the antigenic domain D—Y—K— $X^2$—$X^3$—D in tandem which are joined to a linking sequence (D—Y—K—$X^7$—$X^8$—D—$X^9$—K). In this embodiment, one antigenic domain is immediately adjacent to another antigenic domain, i.e., no intervening spacer domains, and the multiple copies of the antigenic domain are immediately adjacent to the linking sequence when $X^5$ is a bond. The linking sequence contains a single enterokinase cleavable site which is represented by the sequence —$X^7$—$X^8$—D—$X^9$—K, where $X^7$ and $X^8$ may be a bond or an amino acid residue, preferably an aspartate residue, and $X^9$ is a bond or an aspartate residue. In a preferred embodiment, each $X^7$, $X^8$ and $X^9$ is independently an aspartate residue thus resulting in the enterokinase cleavable site DDDDK which is preferably adjacent to the amino terminus of the target peptide. Optionally, the multiple copies of the antigenic domain are joined to the linking sequence by a spacer $X^5$ when $X^5$ is at least one amino acid residue. When $X^5$ is a spacer domain, it is preferred that the amino acid residue(s) of $X^5$ impart one or more desired properties to the identification polypeptide; for example, the amino acids of the spacer domain may be selected to impart a desired folding to the identification polypeptide thereby increasing accessibility to the antibody. In another preferred embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the identification polypeptide; for example, the amino acids represented by $X^2$ and $X^3$ may be selected to impart a desired peptide folding or a desired affinity characteristic for use in affinity purification.

When the identification polypeptide is located at the amino terminus of the target peptide, it is desirable to design the amino acid sequence of the identification polypeptide such that an initiator methionine is present. Accordingly, in a preferred embodiment of the present invention, the identification polypeptide comprises multiple copies of an antigenic domain, a linking sequence containing a single enterokinase cleavage site and generally corresponds to the sequence:

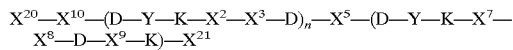

where:

D, Y, and K are their representative amino acids;

$X^{20}$ and $X^{21}$ are independently a hydrogen or a bond;

$X^{10}$ is a bond or an amino acid, if other than a bond, preferably a methionine residue;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a bond or a spacer domain comprising at least one amino acid, if other than a bond, preferably a histidine residue, a glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, -Leu, -Ser, -Lys, -Phe, -Met, Ala, Glu, Ile, Thr, Asp, Asn, Gln, Arg, Cys, and Pro;

$X^9$ is a bond or an aspartate residue; and n is at least 2.

In this embodiment, the amino acid sequence $X^{20}$—(D—Y—K—$X^2$—$X^3$—D)$_n$ represents the multiple copies of the antigenic domain D—Y—K—$X^2$—$X^3$—D in tandem which is flanked by a linking sequence (D—Y—K—$X^7$—$X^8$—D—$X^9$—K) and an initiator amino acid $X^{10}$, preferably methionine. The antigenic domain D—Y—K—$X^2$—$X^3$—D with an initiator methionine is recognized by the M5 antibody. In this embodiment, one antigenic domain is immediately adjacent to another antigenic domain, i.e., no intervening spacer domains, and the multiple copies of the antigenic domain are immediately adjacent to the linking sequence when $X^5$ is a bond. The linking sequence contains an enterokinase cleavable site which is represented by the amino acid sequence —$X^7$—$X^8$—D—$X^9$—K, where $X^7$ and $X^8$ may be a bond or an amino acid residue, preferably an aspartate residue, and $X^9$ is a bond or an aspartate residue. In a preferred embodiment, each $X^7$, $X^8$ and $X^9$ is independently an aspartate residue thus resulting in the enterokinase cleavable site DDDDK (SEQ ID NO: 3) which is preferably adjacent to the amino terminus of the target peptide. Optionally, the multiple copies of the antigenic domain are joined to the linking sequence by a spacer domain $X^5$ when $X^5$ is at least one amino acid residue. When $X^5$ is a spacer domain, it is preferred that the amino acid residue(s) of $X^5$ impart one or more desired properties to the identification polypeptide; for example, the amino acids of the spacer domain may be selected to impart a desired folding to the identification polypeptide thereby increasing accessibility to the antibody. In another preferred embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the identification polypeptide; for example, the amino acids represented by $X^2$ and $X^3$ may be selected to impart a desired peptide folding or a desired affinity characteristic for use in affinity purification.

In another embodiment of the present invention, the identification polypeptide comprises multiple copies of an antigenic sequence, a linking sequence containing a single enterokinase cleavable site and generally corresponds to the sequence:

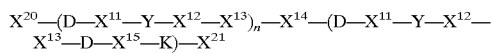

where:
- D, Y and K are their representative amino acids;
- $X^{20}$ and $X^{21}$ are independently a hydrogen or a bond;
- each $X^{11}$ is a bond or an amino acid, preferably L;
- each $X^{12}$ is an amino acid, preferably selected from the group consisting of aromatic amino acid residues and hydrophilic amino acid residues, more preferably a hydrophilic amino acid residue, and still more preferably an aspartate residue;
- each $X^{13}$ is a bond or at least one amino acid, if other than a bond, preferably selected from the group consisting of aromatic amino acid residues and hydrophilic amino acid residues, more preferably a hydrophilic amino acid residue, and still more preferably an aspartate residue;
- $X^{14}$ is a bond or a spacer domain comprising at least one amino acid, if other than a bond, preferably a histidine residue, a glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;
- $X^{15}$ is a bond or an aspartate residue; and
- n is at least 2.

In this embodiment, the amino acid sequence $X^{20}$—(D—$X^{11}$—Y—$X^{12}$—$X^{13}$)$_n$ represents the multiple copies of the antigenic domain D—$X^{11}$—Y—$X^{12}$—$X^{13}$ in tandem which are joined to a linking sequence (D—$X^{11}$—Y—$X^{12}$—$X^{13}$—D—$X^{15}$—K). Additionally, one antigenic domain is immediately adjacent to another antigenic domain, i.e., no intervening spacer domains, and the multiple copies of the antigenic domain are immediately adjacent to the linking sequence when $X^{14}$ is a bond. The linking sequence contains a single enterokinase cleavable site which is represented by the sequence —$X^{12}$—$X^{13}$—D—$X^{15}$—K where $X^{12}$ and $X^{13}$ may be a bond or an amino acid residue, preferably an aspartate residue, and $X^{15}$ is a bond or an aspartate residue. In a preferred embodiment, each $X^{12}$, $X^{13}$ and $X^{15}$ is independently an aspartate residue thus resulting in the enterokinase cleavable site DDDDK (SEQ ID NO:3) which is preferably adjacent to the amino terminus of the target peptide. Optionally, the multiple copies of the antigenic domain are joined to the linking sequence by a spacer $X^{14}$ when $X^{14}$ is at least one amino acid residue. When $X^{14}$ is a spacer domain, it is preferred that the amino acid residue(s) of $X^{14}$ impart one or more desired properties to the identification polypeptide; for example, the amino acids of the spacer domain may be selected to impart a desired folding to the identification polypeptide thereby increasing accessibility to the antibody. In another preferred embodiment, the amino acids of the spacer domain $X^{14}$ may be selected to impart a desired affinity characteristic such as a combination of multiple or alternating histidine residues capable of chelating to an immobilized metal ion on a resin or other matrix.

Target Peptide

In accordance with the present invention, the target peptide may be composed of any proteinaceous substance that can be expressed in transformed host cells. Accordingly, the present invention may be beneficially employed to produce substantially any prokaryotic or eukaryotic, simple or conjugated, protein that can be expressed by a vector in a transformed host cell. Such proteins include enzymes, whether oxidoreductases, transferases, hydrolases, lyases, isomerases or ligases.

The present invention also contemplated the production of storage proteins, such as ferritin or ovalbumin or transport proteins, such as hemoglobin, serum albumin or ceruloplasmin. Also included are the types of proteins that function in contractile and motile systems, for instance, actin and myosin.

The present invention also contemplates the production of proteins that serve a protective or defense function, such as the blood protein fibrinogen. Other protective proteins include the binding proteins, such as antibodies or immunoglobulins that bind to and thus neutralize antigens.

The protein produced by the present invention also may encompass various hormones such as Human Growth Hormone, somatostatin, prolactin, estrone, progesterone, melanocyte, thyrotropin, calcitonin, gonadotropin and insulin. Other such hormones include those that have been identified as being involved in the immune system, such as interleukin 1, interleukin 2, colony stimulating factor, macrophage-activating factor and interferon.

The present invention is also applicable to the production of toxic proteins, such as ricin from castor bean or gossypin from cotton linseed.

Proteins that serve as structural elements may be produced by the present invention; such proteins include the fibrous proteins collagen, elastin and alpha-keratin. Other structural proteins include glyco-proteins, virus-proteins and muco-proteins.

In addition to the above-noted naturally occurring proteins, the present invention may be employed to produce synthetic proteins defined generally as any sequence of amino acids not occurring in nature.

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthesized plasmids having genes coding for many different protein molecules are not commercially available from a variety of sources. The desired DNA also can be produced from mRNA by using the enzyme reverse transcriptase. This enzyme permits the synthesis of DNA from an RNA template.

Preniaration of DNA Expression Vectors

In a ccordance with the present invention, once a gene coding for a target peptide is isolated, synthesized or otherwise obtained, it is joined to a synthetic DNA fragment coding for the identifi cation polypeptide.

The identification polypeptide gene may be synthesized by well-known techniques. For a chosen composition of the identification polypeptide, DNA oligmers encoding for the desired amino acids of the identification polypeptide may be synthesized using a commercially available, automated DNA synthesizer in a manner well known in the art. The techniques and apparatus for synthesizing DNA are common and known in the art; thus, the description and detail to perform this will not be completely set forth herein. Essentially, this process involves obtaining pairs of synthetic oligonucleotides and digesting them with the appropriate restriction endonucleases. This will produce the correct nucleotide sequence encoding for the identification polypeptide tag. After digestion, various DNA fragments are formed with cohesive or "sticky ends." Although there may be many ways in which to perform such construction, the preferred embodiment involves the generation of multiple FLAG® epitope sequence or variations thereof in tandem.

The pair of oligonucleotides used in the construction of the identification polypeptide may be naturally occurring or synthetically generated. It is generally preferred that the specific pairs of oligonucleotides have been synthetically generated to produce the amino acid sequence of the desired identification polypeptide tag. The strands of each oligonucleotide are annealed together and digested with an appropriate restriction endonuclease such as EcoRI and Hind III. After digestion and the creation of the nucleotide cassettes, the sequences can be verified through DNA sequencing.

As discussed below, the synthetic DNA oligmers encoding for the identification polypeptide may be ligated to a DNA sequence encoding for the desired protein and then the combined DNA fragments ligated to an appropriate expression vector to form a cloning vehicle for transformation to an appropriate host cell.

In addition to the target peptide gene and the identification polypeptide gene, if needed, the hybrid DNA fragment may include a ribosome binding site for high level protein translation in a host cell, a translation initiation codon (ATG), and a promoter.

Generally, the genes coding for the target peptide and the identification polypeptide ideally are treated with an appropriate restriction enzyme or are otherwise manipulated to have cohesive termini to facilitate ligation with each other and with a plasmid or other type of cloning vector. The cloning vector is preferably digested with the same restriction endonuclease used to condition the foreign genes in order to form complementary cohesive termini, (i.e., "sticky ends,") prior to ligation with the foreign genes. Alternatively, the use of certain restriction enzymes (e.g., Pvu II, Bal I) may result in the formation of termini without complementary overhanging sequences, commonly referred to as "square" or "blunt ends." The square ends of the plasmid can be joined to the foreign genes with an appropriate ligase. Additionally, various techniques may be used to manipulate the nucleic acids of the blunt ends to form cohesive termini, for instance, linker molecules may be used to add nucleotide bases or appropriate enzymes may be used to remove nucleotide bases from the flush ends. Methods and materials for achieving this are well known in the art.

PCR is also an effective tool for cloning known genes (into blunt or sticky sites). Primers can code for 25–40 bases of known sequence and the resulting PCR product can be cloned into a digested vector having blunt ends by removing any possible 3' overhangs with T4 DNA polymerase. Another method of linking sequences with the use of the PCR reaction is to create restriction sites at the end(s) of the amplified DNA. These restriction sites are easily added to the 5' ends of the primers used for amplification. Digestion of the purified PCR products will produce ends for ligation to other DNA having compatible termini.

It is to be appreciated that digestion of the chosen plasmid with a restriction endonuclease(s) may result in the formation of two or more linear DNA segments. The segment to be used to form the cloning vector, i.e., the segment having the phenotypic identity gene, replicon and the other desired components, may be identified by well-known techniques, such as by gel electrophoresis.

The resulting cloning vector is used to transform a host microorganism. The transformants are isolated and analyzed for the presence of the foreign genes and for the proper orientation of the genes within the vector. The transformants are then multiplied in culture to cause replication of the vector and high level expression of the hybrid polypeptide being sought. In addition, the cloning vectors may be used to transform other strains of the chosen host or other types of hosts for large scale production of the hybrid heterologous polypeptide. Various procedures and materials for preparing recombinant vectors, transforming host cells with the vectors, replicating the vector and expressing polypeptide and proteins are discussed by Old and Primrose, Principles of Gene Manipulation, (2d Ed. 1981).

To carry out the present invention, various cloning vectors may be utilized. Although the preference is the used of a plasmid, the vector may be a bacteriophage or cosmid. If cloning takes place in mammalian or plant cells, viruses can be used as vectors. If a plasmid is employed, it may be obtained from a natural source or artificially synthesized. The particular plasmid chosen should be compatible with the particular cells serving as the host, whether a bacteria such as *Escherichia coli* (*E. coli*), yeast, or other unicellular microorganism. The plasmid should have the proper origin of replication (replicon) for the particular host cell chosen.

In addition, the size of the plasmid must be sufficient to accommodate the hybrid genes coding for both the target peptide and the identification polypeptide, but also of as low a molecular weight as possible. Low molecular weight plasmids are more resistant to damage from shearing and are more readily isolated from host cells. If obtained from natural sources, they are usually present as multiple copies, thereby facilitating their isolation. Also, there is less likelihood that a low molecular weight plasmid has multiple substrate sites for restriction endonucleases.

Another requirement for a plasmid cloning vector is the presence of restriction sites so that appropriate of restriction enzymes can cleave the plasmid for subsequent ligation with the foreign genes without causing inactivation of the replicon. To this end, it would be helpful for the plasmid to have single substrate sites for a large number of restriction endonucleases.

As stated above, there may be intervening amino acid spacer domains between the multiple antigenic domains of the identification polypeptide. By varying the triplet DNA sequence representing specific amino acids (i.e., codons) in the design of these spacer domains, it is possible to create multiple restriction enzyme sites for enzymes that recognize and cleave those designed sequences without changing the amino acid sequence of the encoded identification polypeptide. The use of sequences encoding recognition sites for restriction enzymes having a minimum of 6 bases in the recognition site is preferred thus reducing the chance that multiple restriction sites will be present in both the DNA vector and the DNA sequences encoding the target peptide.

Likewise, a linking sequence is used to join the DNA sequences encoding for the target peptide to the DNA sequences encoding the multiple antigenic domains of the identification polypeptide. By varying the triplet DNA sequence representing specific amino acids in the design of the linking sequence, it is possible to create restriction sites for enzymes that recognize and cleave those designed sequences without changing the amino acid sequence of the encoded identification polypeptide. The use of sequences encoding recognition sites for restriction enzymes having a minimum of 6 bases in the recognition site is preferred; this reduces the chance that multiple restriction enzyme cleavable sites will be present in both the vector and the sequences encoding the target peptide.

Moreover, the plasmid should have a phenotypic property that will enable the transformed host cells to be readily identified and separated from cells which do not undergo transformation. Such phenotypic selection genes can include genes providing resistance to a growth inhibiting substance, such as an antibiotic. Plasmids are not widely available that include genes resistant to various antibiotics, such as tetracycline, streptomycin, sulfa drugs, penicillin, and ampicillin. When host cells are grown in a medium containing one of these antibiotics, only transformants having the appropriate antibiotic resistance gene will survive.

Rather than utilizing a gene resistance to a growth inhibiting compound to identify transformed host cells, phenotypic selection genes can also include those that provide growth factor to permit transformed cells to propagate in a medium which lacks the necessary growth factor for the host cells. For instance, for yeast auxotrophs, such growth factors include tryptophan or leucine.

Alternatively, it is preferred that a DNA sequence encoding a signal peptide be joined to the sequences encoding the identification polypeptide and the target peptide. The use of a secreted signal sequence will also enable the transformed host cells to be readily identified and separated from cells which do not undergo transformation. Secretion signals are relatively short in most species, generally comprised of 16–40 amino acids. Additionally, signal sequences from bacterial or eukaryotic genes are highly conserved in terms of function. Although the DNA sequences encoding for these signal peptides are not highly conserved, many of these signal sequences have been shown to be interchangeable. See Grey, G. L. et al., *Gene* 39:247 (1985).

Transformation of the Recombinant Plasmid

Once a suitable DNA vector encoding the desired hybrid polypeptide has been constructed, the vector is introduced into the desired host cell. Although the host cell may be any appropriate prokaryotic or eukaryotic cell, preferably it is a well-defined bacteria, such as *E. coli* or a yeast strain. Both such hosts are readily transformed and capable of rapid growth in fermentation cultures. In place of *E. coli*, other unicellular microorganisms can be employed, for instance fungi and algae. In addition, other forms of bacteria such as salmonella or pneumococcus may be substituted for *E. coli*. Whatever host is chosen, it should be one that does not contain a restriction enzyme that would cleave the recombinant plasmid and that has the necessary biochemical pathways for phenotypic expression and other functions for proper expression of the hybrid polypeptide.

DNA molecules are transfected into prokaryotic and eukaryotic hosts using standard protocols known in the art. Briefly, the prokaryotic host cells are made competent by treatment with calcium chloride solutions (competent bacteria cells are commercially available and are easily made in the laboratory). This treatment permits the uptake of DNA by the bacterial cell. Another means of introducing DNA into bacterial cells is electroporation in which an electrical pulse is used to permit the uptake of DNA by bacterial cells. Likewise, standard protocols such as calcium phosphate-DNA co-precipitation, DEAE-dextran-mediated transfection, electroporation, microinjection, lipofection, protoplast fusion, retroviral infection, particle bombardment (e.g., biolistics) are commonly used for the introduction of DNA molecules into eukaryotic hosts, including yeast and higher eukaryotes.

In transformation protocols, only a small portion of the host cells are actually transformed, due to limited plasmid uptake by the cells. Thus, before transformants are isolated, the host cells used in the transformation protocol typically are multiplied in an appropriate medium. The cells that actually have been transformed can be identified by placing the original culture on agar plates containing a suitable growth medium containing the phenotypic identifier, such as an antibiotic. Only those cells that have the proper resistant gene will survive. Cells from the colonies that survive can be lysed and then the plasmid isolated from the lysate. The plasmid thus isolated can be characterized to determine if the cointegrate genes are ligated in the correct orientation, by digestion with restriction endonucleases and subsequent gel electrophoresis or both other standard methods.

Once transformed cells are identified, they can be multiplied by established techniques, such as by fermentation. In addition, the recovered cloned recombinant plasmids can be used to transform other strains of bacteria or other types of host cells for high scale replication and expression of the hybrid polypeptide.

Purification of Hybrid Polypeptide

The hybrid polypeptide molecules expressed by the transformed host cells are separated from the culture medium, other cellular material, etc. preferably by an affinity chromatography process. To this end, antibodies against the antigenic domains of the identification polypeptide of the hybrid polypeptide must be generated for use on a column matrix. To produce such antibodies, the identification polypeptide is first synthesized and then used to immunize an appropriate animal for production of an antibody against the identification polypeptide. Such methods for producing antibodies are taught in U.S. Pat. No. 4,851,341, incorporated herein by reference. The antibody can be identified by an enzyme-linked immunosorbent assay (ELISA) or other appropriate assay. A monoclonal then can be produced by hybridoma techniques. Preferred antibodies are the FLAG® monoclonal antibodies M1, M2 and M5. After purification, the antibody or antibodies are bound to the column matrix and then an extract from the transformed host cells applied to the column to isolate the hybrid polypeptide. The hybrid polypeptide is eluted from the column, for instance, by competition from free identification polypeptide.

Additionally, if the identification polypeptide contains histidine, glycine or combinations of multiple or alternating histidine residues, Immobilized Metal Ion Affinity Chromatography (IMAC) may be used as an alternative method to isolate and purify target peptides. When a hybrid polypeptide containing the target peptide and the identification polypeptide is produced and passed through a column containing immobilized metal ions, the hybrid polypeptide will chelate immobilized metal ions. The hybrid polypeptide should chelate to the immobilized metal ions for a sufficient amount of time to allow it to be separated from other materials. Once the hybrid polypeptide is bound to the metal ion resin, the hybrid polypeptide may be released by protonation of its associated metal ion-binding ligand. Dissociation is achieved by lowering the pH of the surrounding buffer medium, a common method known in the art for eluting bound proteins. The target peptide may then be cleaved from the identification polypeptide as further discussed herein.

Other methods may be used to detect, monitor or isolate target peptides. Such methods include immunoprecipitation and Western blotting as are described in "Principles and Practice of Immunoassay," Price and Newman, eds., Stochton Press, 1991. The use of immunoprecipitation as a sensitive and specific technique to detect and quantitate target antigen in mixtures of proteins is known to one skilled in the art. See Molecular Cloning, A Laboratory Manual, 2d Edition, Maniatis, T. et al. eds. (1989) Cold Spring Harbor Press. Briefly, antibodies, preferably FLAG® monoclonal antibodies, M1, M2 or M5 capable of binding to the antigenic domains of the identification polypeptide may be used to detect the proteins using immunoprecipitation tests. As described above, cells are transformed with the identification polypeptide, grown in culture media, and lysed to obtain a solution of tagged proteinaceous material produced by the cells. This solution is incubated with a solution of a monoclonal antibodies, and any complex between identification polypeptide labeled protein formed in the cell and the antibodies are determined by precipitation. The protein/antibody complex can then be isolated from the precipitate. The presence of the labeled protein is then confirmed by usual analytical methods, e.g., SDS polyacrylamide gel electrophoresis with fluorography, under conditions dissociating the protein/antibody complex.

Additionally, Western blotting is another immunoassay technique used to detect the target peptide. Generally, small quanities of a target peptide are electrophoresed on a polyacrylamide gel and transferred (by blotting) to a polymer sheet or membrane. The membrane is then incubated with a first antibody, preferably a FLAG® monoclonal antibody which may bind to the antigenic domains of the identification polypeptide. The membrane containing the antibody-antigen is then incubated with a second labeled antibody specific for the first antibody. The protein tagged with the identification polypeptide may be detected and visualized by known methods such as autoradiography.

Separation of Mature Protein from Purified, Hybrid Identification Polypeptide/Protein Molecules Unless removed while still bound to the affinity column or matrix, the identification polypeptide may be cleaved from the protein molecule and the protein molecule separated from the identification polypeptide, thereby resulting in a purified protein. This is accomplished by first suspending the hybrid identification polypeptide/protein molecules in buffer. Thereafter, the proteolytic enzyme or other chemical proteolytic agent that is specific for the amino acid residues composing the linking portion of the identification polypeptide is added to the suspension. The enzyme may be coupled to a gel matrix to prevent contamination of the product solution with the enzyme. As discussed above, the proteolytic enzyme or chemical proteolytic agent cleaves the hybrid polypeptide between the adjacent amino acid residues of the linking portion of the identification polypeptide and the protein molecule. Also as also noted above, as a nonlimiting example, the linking amino acids may be composed of the sequence: Asp-Asp-Asp-Asp-Lys (SEQ ID NO:3). This particular sequence of amino acids is only known to occur naturally in the protein trypsinogen, the substrate for bovine mucosal enterokinase. Thus, by use of this particular amino acid sequence it is highly unlikely that enzyme cleavage of the hybrid identification polypeptide protein molecules would also cause cleavage of the protein molecule itself.

After incubation, the desired protein is purified as follows. If the proteolytic agent is an enzyme attached to a gel matrix, the suspension is centrifuged and the pellet (containing the enzyme-gel conjugate) is discarded. The supernatant contains only the protein product, the cleaved identification polypeptide and possibly small amounts of uncleaved peptide/protein molecule, in addition to buffer salts. In the case of chemical cleavage agents, there would be no gel centrifugation step, and the solution would contain a residual chemical agent and by-products of the chemical agent in addition to the protein product, identification polypeptide and small amounts of uncleaved peptide/protein molecule.

Most of the above-mentioned contaminating substances are much smaller than the protein product and can be efficiently removed by simple means, such as gel filtration or dialysis. Only the uncleaved identification polypeptide/protein molecule would remain to contaminate the protein product after such steps. To remove the polypeptide/protein molecule from the protein product, the mixture is passed over a second affinity column, which column has attached to it the same antibody specific for the identification polypeptide as was used for removal of the peptide/protein molecule from the original production medium. The antibody binds the unwanted polypeptide/protein molecule, and the eluate from the column contains only the desired product protein, now free of all contaminants.

If a soluble enzyme is used for proteolytic cleavage, then the protein product may contain small amounts of the enzyme, which can be removed by passing the solution over an affinity column containing an immobilized substrate for the enzyme. The enzyme is thereby bound to the column and the desired protein molecules allowed to pass through.

As noted above, some protein products will possess the desired enzymatic activity with the identification polypeptide still attached thereto. As a consequence, the identification polypeptide need not be cleaved from the protein molecule, thus the above described cleave and subsequent purification steps need not be performed.

Moreover, in situations in which the identification polypeptide remains attached to the protein molecule, the linking portion of the identification polypeptide is not needed. Instead, the identification polypeptide can be composed solely of the antigenic domains. In this situation the construction and method of preparing the DNA expression vectors, detailed above, can be appropriately modified.

The following examples are intended to illustrate but not limit the present invention.

EXAMPLES

Example 1 p3XFLAG-CMV-7 Construction

Materials and Methods

Construction of P3XFLAG-CMV-7

P3XFLAG-CMV-7 was constructed from the mammalian expression vector, pCMV-5. The triple FLAG sequence was constructed from two pairs of complimentary oligonucleotides. The first pair of oligonucleotides was synthesized as follows:

5'GAAGAATTCACCATGGACTACAAAGAC-CATGACGGTGATTATAAAGATCAT GAT3' (SEQ ID NO: 8) and 5'ATCATGATCTTTATAATCACCGTCATG-GTCTTTGTAGTCCATGGTGAATTCT TC3' (SEQ ID NO: 9). The second pair was synthesized with the following sequence:

5'GAAGATATCGATTACAAGGATGACGAT-GACAAGCTTGGG3' (SEQ ID NO: 10) and 5'CCCAAGCTTGTCATCGTCATCCTTG-TAATCGATATCTTC3' (SEQ ID NO: 11).

The first pair of oligonucleotides were annealed together and digested with EcoR I. The second pair of oligonucleotides were annealed together and digested with EcoR V and Hind III. The two pairs of digested nucleotide cassettes were ligated into CMV-5, which has been double digested with EcoR I and Hind III. The sequence was verified by DNA sequencing.

pFLAG-CMV7-BAP Construction

A modified version of the *E. coli* pho A gene for which the leader sequence and the N-terminal four amino acids of the mature enzyme were deleted, was subcloned into the vector p3XFLAG-CMV-7. The modified sequence was cut from pFLAG-ATS-BAP by double digestion with Hind III and Bgl II. The fragment was then cloned into p3XFLAG CMV-7 which had been double digested with Hind III and Bam HI to generate p3XFLAG-CMV-7-BAP. The nucleotide sequence at the N-terminus of the phoA coding region was verified.

Triple FLAG-ATS-BAP Construction

Two oligonucleotides encoding the sense and anti-sense strand for the triple FLAG sequence were synthesized, 5' phosphorylated with T4 polynucleotide kinase, and annealed together. pFLAG-ATS-BAP was digested with Nde I and Hind III and the vector purified by gel electrophoresis. The annealed cassette was ligated to the double digested pFLAG-ATS-BAP vector with T4 DNA ligase and the reaction carried out overnight at 16° C. for 16 hours. The ligation was enriched by digestion with Nru I and then transformed into E. coli DH5α. Clones were isolated and verified by sequencing.

Results

Applicants have constructed a vector for expression of proteins in mammalian host cells using a modified version of the FLAG expression system, which contains 3XFLAG sequences in tandem (FIG. 1). This construct was designed to improve the detection limit of expressed proteins in mammalian host cells. The first two flag peptides are modified FLAG sequences. The original FLAG® epitope is Asp-Tyr-Lys-Asp-Asp-Asp-Asp-Lys (SEQ ID NO: 1) while the first two flag recognition sequences is Asp-Tyr-Lys-Asp-His-Asp (SEQ ID NO: 12) with either a Gly or Ile spacer domain between the two sequences. These alternative sequences arise from phage display studies in which a different binding motif was determined. See Miceli et al., *J. Immunological Methods* 167:279–287 (1994). This allows the introduction of additional FLAG antibody binding sites without the addition of extra enterokinase recognition/cleavable sites.

The p3XFLAG-CMV-7 expression vector contains the human cytomegalovirus promoter region necessary for constitutive expression of cloned genes in many mammalian cell lines. The Kozak consensus sequence is provided in the vector along with a multiple cloning site, which allows for a variety of cloning strategies. The multiple cloning site is compatible with the other existing CMV mammalian expression vectors. In addition the expression vector contains the SV40 origin of replication for efficient high-level transient expression and a DNA segment from the human growth hormone containing transcriptional termination sequence and polyadenylation signals. p3XFLAG-CMV-7 contains the β-lactamase gene for selection of the plasmid in E. coli.

Example 2

Bacterial Expression of p3XFLAG-ATS-BAP and Protein Purification

Materials and Methods

E. coli BL21 (DE3) were transformed with the expression plasmid containing the triple FLAG BAP construct made according to the methods of Example 1. Cells were grown in terrific broth containing 100 μg/ml ampicillin at 37° C. with agitation. The culture was grown to an $OD_{600}$=4.0 and then induced with IPTG at a final concentration of 1 mM. The cell culture was grown for an additional 3 hours at 37° C. and then harvested by centrifugation. The cell pellet was resuspended in 50 mM Tris-HCl pH 8.0 and the cells disrupted by sonication and cellular debris removed by centrifugation. The supernatant was applied to M2 affinity gel was equilibrated with 50 mM Tris-HCl pH 8.0, 150 mM NaCl (TBS). The resin was washed with 20 bed volumes of TBS and then the triple FLAG BAP was eluted with five column volumes of 0.1 M Glycine pH 3.5. The eluted protein was pooled and adjusted to pH 7.5 with 1.0 M Tris-HCl pH 8.0. Protein content was determined by both Bradford and by absorbance using $\epsilon_{280}$=0.7 ml/mg.

Western Blot

Purified 3XFLAG-BAP and N-BAP were diluted with to 2× Laemlli buffer, boiled for five minutes and then placed on ice. Samples were resolved on a 15% SDS-PAGE using the method of Laemlli (Laemli, V., *Nature*, 227:680–685 (1970)) and then transferred to nitrocellulose membranes. The membrane was blocked with phosphate buffered saline containing 3% non-fat dry milk for 1 hour and then rinsed three times in TBS, 0.05% Tween 20 (TBS-T). The membrane was incubated with M2 antibody at a final concentration of 10 μg/ml for 30 minutes in TBS-T and then rinsed three times in TBS-T. The membrane was then incubated for 30 minutes with a goat anti-rabbit IgG (whole molecule) Horseradish peroxidase(HRP) conjugate diluted 1:10,000 in TBS-T then rinsed three times in TBS-T. The FLAG tagged protein were detected with the HRP conjugates and visualized by chemilumenescent detection using ECL (Amersham) and Kodak X-Omat MR film according to manufacturer's directions with exposures from 1 to 30 minutes.

Results

To address whether a triple FLAG fusion protein produces a more sensitive response then the traditional FLAG® epitope, a triple FLAG version of bacterial alkaline phosphatase was constructed for expression in *E. coli*. The vector p3XFLAG-ATS-BAP was transformed into *E. coli* and the 3XFLAG-BAP expressed and purified as described in material and methods. In addition, an N-FLAG-BAP containing the traditional FLAG® epitope (DYKDDDDK) was also expressed and purified. Comparison of the sensitivity of the single versus the triple FLAG-BAP was demonstrated by western blot analysis as described above. FIG. 4 shows the western blot of purified single and triple flag probed with M2 antiFLAG antibody and detected by chemiluminescence. The results clearly indicate that there is a 10-fold increase in detection limit of the triple FLAG-BAP compared to the single FLAG-BAP fusion protein. Applicants were able to detect 500 picograms of purified 3 X Flag bacterial alkaline phosphatase with exposures as short as 1 minute. With increased exposure time, detection as low as 100 picograms has been achieved but with increased background. Applicants have also demonstrated at least a 10-fold increase detection in both dot blot and ELISA assay.

Example 3

Expression of 3× Bacterial Alkaline Phosphotase in COS-7 cells

Materials and Methods

Transfection of COS-7 Cells with p3XFLAG-CMV-7-BAP

COS-7 cells were cultured on 35 $mm^2$ plates in Dulbecco's Modified Eagles Medium (DME), containing 10% fetal bovine serum, 4 mM L-glutamine, 5 μg/ml gentamycin. Cells were grown at 37° C. in a humidified $CO_2$ incubator with 5% $CO_2$. Transfection of the p3XFLAG-CMV7-BAP plasmid was accomplished using Lipofectamine (Life Technologies Inc., Gaithersburg Md.) according manufacturer's directions. Two micrograms of vector DNA was used for the transfection. Immunostaining was done 72 hour post transfection.

Immunostaining

At 72 hours post induction, the cells were washed with 50 mM Tris-HCl pH 7.4, 150 mM NaCl (TBS). The cells were fixed with 1:1 (v/v) methanol-acetone mixture for 1 minute. The fixed cells were washed four times with TBS and then incubated with 10 µg/ml M2 antibody-HRP conjugate in TBS for 1 hour. Cells were washed with TBS five times and the M2 antibody-HRP conjugate visualized with freshly prepared 0.01 mg/ml o-dianisidine, 0.015% hydrogen peroxide in TBS. Cells were stained for approximately 15 minutes.

Figure 2A:
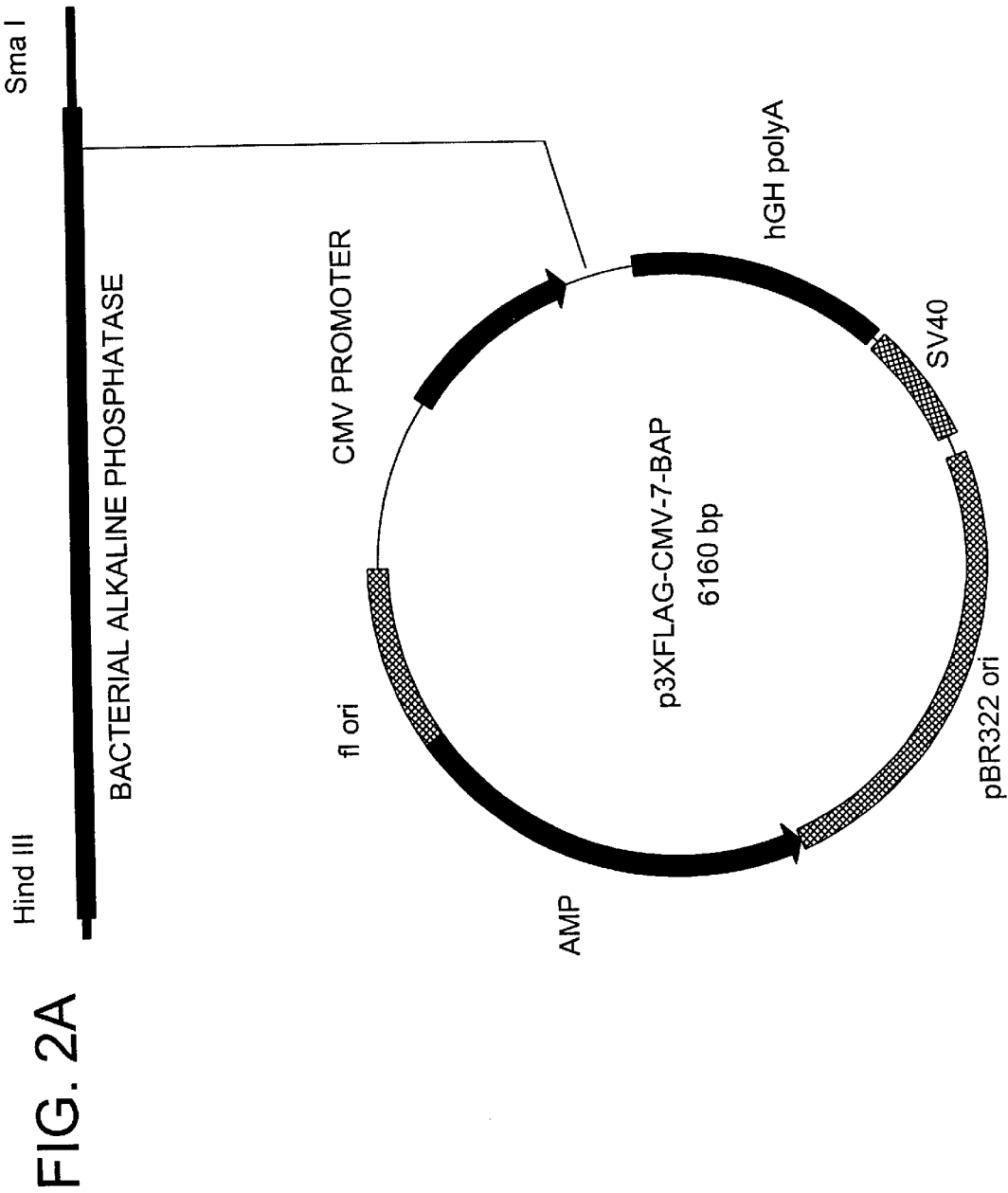
FIG. 2A is a vector map of p3XFLAG-CMV-7-BAP showing insertion of the phoA coding region into P3xflag-CMV-7.
Figure 2B:
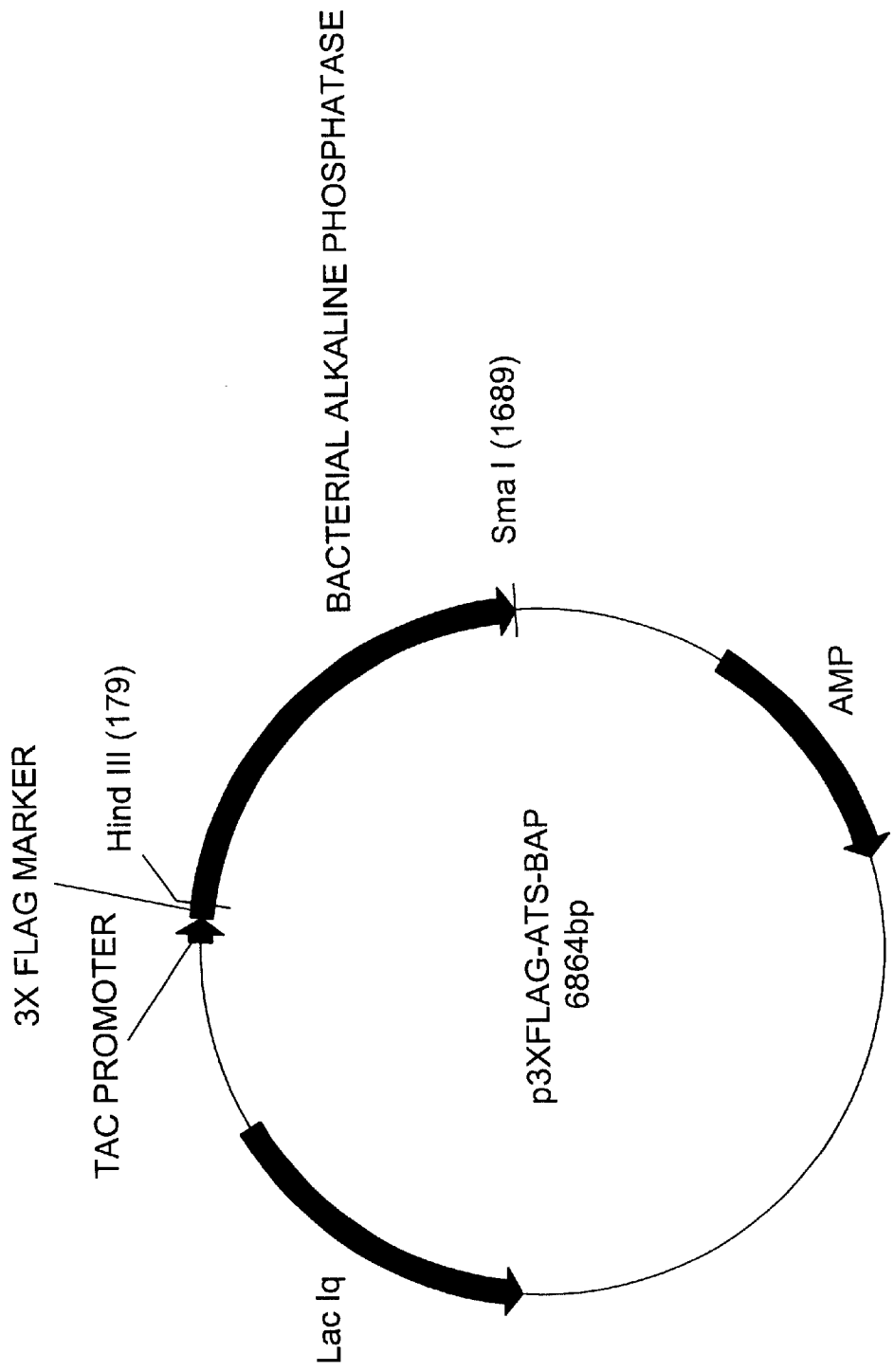
FIG. 2B is a vector map of p3XFLAG-ATS-BAP showing insertion of the phoA coding region into pFLAG-ATS-BAP.
Figure 3:
FIG. 3 is a Western Blot of purified 3XFLAG-BAP (A) and N-FLAG-BAP (B) using anti-FLAG M2 antibody. Lane (s) (1) 0.5 ng; (2) 1.0 ng; (3) 2.0 ng; (4) 5.0 ng; and (5) 10 ng. Amounts shown are the amounts loaded onto the gel before transfer.

Results p3XFLAG-CMV-7-BAP (FIG. 2) was transfected into COS-7 cells as described in the materials and methods. At 72 hours post transfection, the cells were analyzed by immunostaining using an anti-FLAG M2 HRP conjugate. Light microscopy of cells detected with M2 antibody, and visualized with o-dianisidine, is shown in FIG. #3.

Discussion

Applicants have created a mammalian expression plasmid containing multiple FLAG® epitopes in tandem, p3X FLAG CMV-7, designed for intracellular expression with increased sensitivity of detection. This vector contains the cytomegalvirus (CMV) promoter and SV40 origin of replication for efficient expression in COS-7 cells. Moreover, detection of triple FLAG tagged BAP expressed and purified from E. coli was compared to single FLAG tagged BAP.

The FLAG® epitope tag has been effectively used to detect and purify protein in mammalian and bacterial systems. Applicants have demonstrated that the presence of three FLAG epitopes significantly increases the detection limit of purified bacterial alkaline phosphatase. Moreover, the 3X FLAG-BAP cannot be eluted from anti-FLAG M2 affinity gel by competition with the original FLAG® peptide. However, 3XFLAG-BAP and the 1XFLAG-BAP can be competitively eluted from the anti-FLAG M2 affinity gel using 3X FLAG peptide. The p3XFLAG-CMV-7 vector was designed for expression and detection of heterologous proteins in mammalian cells and is compatible with existing pFLAG-CMV vectors thus allowing for easy subcloning between vectors containing the single FLAG and the triple FLAG. The immunostaining results show that expression of the pho A gene in COS-7 cells is not significantly perturbed by addition of the 3X FLAG sequence.

The M2 antibody reacts with the alternate FLAG in the 3X FLAG sequence. In contrast, M5 antibody fails to show the increased sensitivity that the M2 antibody demonstrates. Recent results using phage display have demonstrated that the critical residues for M2 binding and M5 binding are slightly different. M2 antibody prefers the sequence Asp-Tyr-Lys-XXX-XXX-Asp-XXX-XXX (SEQ ID NO: 13) while M5 prefers Asp-Tyr-XXX-XXX-Asp-Asp-XXX-XXX (SEQ ID NO: 14). The triple FLAG sequence Asp-Tyr-Lys-Asp-His-Asp clearly favors the binding of M2 over that of M5 or even M1 antibody.

Example 4

Analysis of the FLAG M2 Antibody Binding to Multiple FLAG Epitopes

Materials and Methods

Thermodynamic analysis of the M2 antibody binding to the FLAG epitopes was measured by isothermal titration calorimetry using an OMEGA calorimeter (Microcal). All samples were dialyzed against PBS containing 0.05% sodium azide and degassed prior to the measurements. All measurements were made at 25° C. The concentration of M2 antibody was between 15 and 50 uM depending upon which samples were used. The concentration of the titrants were 605 uM for the 1X BAP, 1110 uM for the 1X FLAG peptide, 400 uM for the 3X BAP, and 580 uM for the 3X FLAG peptide. Injections were carried out every 2.5 to 3.0 minutes which was sufficient for baseline to be achieved with injection volumes ranging from 4 to 11 uL. Injections were carried out over a 4 to 10 second period while stirring at 400 rpm.

Data analysis and fitting were performed using the Origin software supplied by MicroCal. The enthalpies were obtained by numerical integration of the data and subtraction of the heats of dilution. Values of Ka, n the number of binding sites were determined by fitting the data to a theoretical curve with only the enthalpy was held constant during the fitting process.

Results and Discussion

In the case of the 1X FLAG system Ka was small enough so that the value r<1000 where r=KaMt(0) with Mt(0) is the initial concentration of M2 antibody in cell. For the 3X FLAG system, the Ka was large enough such that r>1000 indicating a tight binding system and thus accurate measurements about the Ka can not be determined.

Applicants have demonstrated that placing three epitopes in tandem produces an increase in the association constant that is well over an order of magnitude larger then that of one epitope, as shown in Table 1.

TABLE 1

|    | 1XBAP      | 1X Peptide | 3XBAP      | 3X Peptide |
|----|------------|------------|------------|------------|
| Ka | 1.69E + 07 | 1.17E + 07 | 2.09E + 08 | 3.66E + 08 |

The values Ka for the single epitope peptide and the single epitope BAP are similar which allude to comparable binding mechanisms. For the three epitope systems, both the peptide epitope and the epitopes on BAP values of Ka also suggesting comparable mechanisms. The increased level of detection of observed in the triple FLAG system is due primarily to an increase in the association constant.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the present invention.

We claim:

1. A DNA segment encoding for an identification polypeptide for use in purifying a target peptide wherein said identification polypeptide comprises:

a. multiple copies of an antigenic domain joined together in tandem, each of the antigenic domains comprising no more than twenty amino acid residues with at least two different amino acid residues; and b. a linking sequence between the multiple copies of the antigenic domain and the target peptide molecule, the linking sequence comprising a cleavable site wherein the cleavable site is not duplicated within or interposed between the multiple copies of the antigenic domain.

2. The DNA segment of claim 1 wherein the amino acid sequence of each such antigenic domain comprises at least one-half hydrophilic amino acid residues.

3. The DNA segment of claim 2 wherein the amino acid sequence of each such antigenic domain comprises at least three-fourths hydrophilic amino acid residues.

4. The DNA segment of claim 1 wherein the amino acid sequence of each such antigenic domain comprises at least one amino acid selected from the group of hydrophilic amino acid residues and at least one amino acid selected from the group of aromatic amino acid residues.

5. The DNA segment of claim 4 wherein the amino acid sequence of each such antigenic domain comprises no more than ten amino acid residues with at least two different amino acid residues.

6. The DNA segment of claim 4 wherein the amino acid sequence of each such antigenic domain comprises no more than six amino acid residues with at least two different amino acid residues.

7. The DNA segment of claim 1 wherein the amino acid sequence of each such antigenic domain comprises a plurality of amino acids of the group consisting of arginine, proline, glutamic acid, aspartic acid, phenylalanine and isoleucine.

8. The DNA segment of claim 1 wherein said cleavable site further comprises an amino acid sequence being cleavable by a sequence-specific proteolytic agent at a specific amino acid residue adjacent to the protein molecule, wherein the sequence-specific proteolytic agent is selected from the group consisting of enterokinase, Factor Xa and thrombin.

9. The DNA segment of claim 6 wherein said cleavable site is an enterokinase recognition site.

10. The DNA segment of claim 1 wherein said identification polypeptide further comprises a spacer domain comprising at least one amino acid residue interposed between any two or more antigenic domains of said multiple copies of the antigenic domain or between the multiple copies of the antigenic domain and the linking sequence.

11. The DNA segment of claim 10 wherein the amino acid sequence of said spacer domain is selected from the group consisting of hydrophilic amino acid residues.

12. The DNA segment of claim 10 wherein said spacer domain further comprises at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

13. The DNA segment of claim 10 wherein the amino acid sequence of said spacer domain comprises isoleucine.

14. The DNA segment of claim 1 wherein said identification polypeptide further comprises a metal chelating sequence joined to said multiple copies of the antigenic domain, wherein the metal chelating sequence comprises at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

15. The DNA segment of claim 1 wherein said identification polypeptide further comprises a multiple cloning site comprising multiple restriction enzyme recognition sites.

16. The DNA segment of claim 1 wherein the identification polypeptide further comprises the amino acid sequence

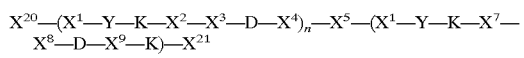

where:
D, Y and K are their representative amino acids;
$X^{20}$ and $X^{21}$ are independently a hydrogen or a bond;
each $X^1$ and $X^4$ is independently a bond or at least one amino acid residue selected from the group consisting of aromatic amino acid residues and hydrophilic amino acid residues;
each $X^2$, $X^3$, $X^7$ and $X^8$ is independently an amino acid residue selected from the group consisting of aromatic amino acid residues and hydrophilic amino acid residues;
$X^5$ is a bond or a spacer domain comprising at least one amino acid, at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

$X^9$ is a bond or an aspartate residue; and
n is at least 2.

17. The DNA expression vector of claim 16 wherein each $X^2$ and $X^3$ is independently a metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

18. The DNA segment of claim 1, wherein the identification polypeptide further comprises the amino acid sequence

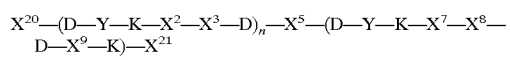

where:
D, Y, K are their representative amino acids;
$X^{20}$ and $X^{21}$ are independently a hydrogen or a bond;
each $X^2$, $X^3$, $X^7$ and $X^8$ is independently an amino acid residue selected from the group consisting of aromatic amino acid residues and hydrophilic amino acid residues;
$X^5$ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;
$X^9$ is a bond or an aspartate residue; and
n is at least 2.

19. The DNA segment of claim 18 wherein each $X^2$ and $X^3$ is independently a metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

20. The DNA segment of claim 6, wherein the identification polypeptide further comprises the amino acid sequence

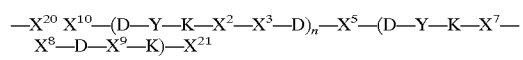

where:
D, Y, and K are their representative amino acids;
$X^{20}$ and $X^{21}$ are independently a hydrogen or a bond;
$X^{10}$ is a bond, any amino acid residue or a methionine residue;
each $X^2$, $X^3$, $X^7$ and $X^8$ is independently an amino acid residue selected from the group consisting of aromatic amino acid residues and hydrophilic amino acid residues;
$X^5$ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

X⁹ is a bond or an aspartate residue; and n is at least 2.

21. The DNA segment of claim 20 wherein each X² and X³ is independently a metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

22. The DNA segment of claim 1, wherein the identification polypeptide further comprises the amino acid sequence

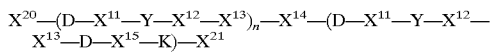

where:

D, Y and K are their representative amino acids;

X²⁰ and X²¹ are independently a hydrogen or a bond;

each X¹¹ is a bond, any amino acid, or a lysine residue;

each X¹² is an amino acid selected from the group consisting of aromatic amino acid residues and hydrophilic amino acid residues;

each X¹³ is a bond or at least one amino acid selected from the group consisting of aromatic amino acid residues and hydrophilic amino acid residues;

X¹⁴ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

X¹⁵ is a bond or an aspartate residue; and n is at least 2.

23. A DNA expression vector comprising DNA coding for a hybrid polypeptide comprising a target polypeptide and an identification polypeptide comprising:

a. multiple copies of an antigenic domain joined together in tandem, each of the antigenic domains comprising no more than twenty amino acid residues with at least two different amino acid residues; and b. a linking sequence between the multiple copies of the antigenic domain and the target peptide molecule, the linking sequence comprising a cleavable site wherein the cleavable site is not duplicated within or interposed between the multiple copies of the antigenic domain.

24. The DNA expression vector of claim 23 wherein the amino acid sequence of each such antigenic domain comprises at least one-half hydrophilic amino acid residues.

25. The DNA expression vector of claim 24 wherein the amino acid sequence of each such antigenic domain further comprises at least three-fourths hydrophilic amino acid residues.

26. The DNA expression vector of claim 23 wherein the amino acid sequence of each such antigenic domain comprises at least one amino acid selected from the group of hydrophilic amino acid residues and at least one amino acid selected from the group of aromatic amino acid residues.

27. The DNA expression vector of claim 26 wherein the amino acid sequence of each such antigenic domain comprises no more than ten amino acid residues with at least two different amino acid residues.

28. The DNA expression vector of claim 26 wherein the amino acid sequence of each such antigenic domain comprises no more than six amino acid residues with at least two different amino acid residues.

29. The DNA expression vector of claim 23 wherein the amino acid sequence of each such antigenic domain comprises a plurality of amino acids of the group consisting of arginine, proline, glutamic acid, aspartic acid, phenylalanine and isoleucine.

30. The DNA expression vector of claim 23 wherein said cleavable site further comprises an amino acid sequence being cleavable by a sequence-specific proteolytic agent at a specific amino acid residue adjacent to the protein molecule wherein the sequence-specific proteolytic agent is selected from the group consisting of enterokinase, Factor Xa and thrombin.

31. The DNA expression vector of claim 30 wherein said cleavable site is an enterokinase recognition site.

32. The DNA expression vector of claim 23 wherein said identification polypeptide further comprises a spacer domain comprising at least one amino acid residue interposed between any two or more antigenic domains of said multiple copies of the antigenic domain or between the multiple copies of the antigenic domain and the linking sequence.

33. The DNA expression vector of claim 32 wherein the amino acid sequence of said spacer domain is selected from the group consisting of hydrophilic amino acid residues.

34. The DNA expression vector of claim 32 wherein said spacer domain further comprises at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

35. The DNA expression vector of claim 32 wherein the amino acid sequence of said spacer domain comprises isoleucine.

36. The DNA expression vector of claim 23 wherein said identification polypeptide further comprises a metal chelating sequence joined to said multiple copies of the antigenic domain, said metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

37. The DNA expression vector of claim 23 wherein said identification polypeptide further comprises a multiple cloning site comprising of multiple restriction enzyme recognition sites.

38. The DNA expression vector of claim 23, wherein the identification polypeptide further comprises the amino acid sequence

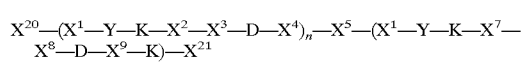

where:

D, Y and K are their representative amino acids;

X²⁰ and X²¹ are independently a hydrogen or a bond;

each X¹ and X⁴ is independently a bond or at least one amino acid residue selected from the group consisting of aromatic amino acid residues and hydrophilic amino acid residues;

each $X^2$, $X^3$, $X^7$ and $X^8$ is independently an amino acid residue selected from the group consisting of aromatic amino acid residues and hydrophilic amino acid residues;

$X^5$ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

$X^9$ is a bond or an aspartate residue; and n is at least 2.

39. The DNA expression vector of claim 38 wherein each $X^2$ and $X^3$ is independently a metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Val, Leu, Ser, Lys, Phe, Met, Ala, Glu, Ile, Thr, Asp, Asn, Gln, Arg, Cys, and Pro.

40. The DNA expression vector of claim 23 wherein the identification polypeptide further comprises the amino acid sequence

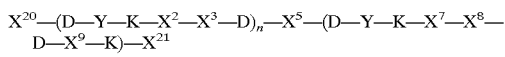

where:

D, Y, K are their representative amino acids;

$X^{20}$ and $X^{21}$ are independently a hydrogen or a bond;

each $X^2$, $X^3$, $X^7$ and $X^8$ is independently an amino acid residue selected from the group consisting of aromatic amino acid residues and hydrophilic amino acid residues;

$X^5$ is a bond or a spacer domain comprising at least one amino acid, at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

$X^9$ is a bond or an aspartate residue; and n is at least 2.

41. The DNA expression vector of claim 40 wherein each $X^2$ and $X^3$ is independently a metal chelating sequence comprising at least one histidine residue, at least one glycine residue or a combination of multiple or alternating histidine residues, said combination comprising His-Gly-His or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro.

42. The DNA expression vector of claim 23 wherein the identification polypeptide further comprises the amino acid sequence

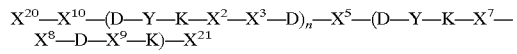

where:

D, Y, and K are their representative amino acids;

$X^{20}$ and $X^{21}$ are independently a hydrogen or a bond;

$X^{10}$ is a bond, any amino acid, or a methionine residue;

each $X^2$, $X^3$, $X^7$ and $X^8$ is independently an amino acid residue selected from the group consisting of aromatic amino acid residues and hydrophilic amino acid residues;

$X^5$ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

$X^9$ is a bond or an aspartate residue; and n is at least 2.

43. The DNA expression vector of claim 23 wherein the multiple copies of the antigenic domain comprise the amino acid sequence

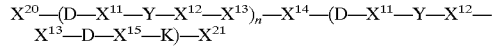

where:

D, Y and K are their representative amino acids;

$X^{20}$ and $X^{21}$ are independently a hydrogen or a bond;

each $X^{11}$ is a bond, any amino acid, or a lysine residue;

each $X^{12}$ is an amino acid selected from the group consisting of aromatic amino acid residues and hydrophilic amino acid residues;

each $X^{13}$ is a bond or at least one amino acid selected from the group consisting of aromatic amino acid residues and hydrophilic amino acid residues;

$X^{14}$ is a bond or a spacer domain comprising at least one amino acid, at least one histidine residue, at least one glycine residue or a combination of multiple or alternating histidine residues, said combination comprising His-Gly-His, or —(His-X)$_m$—, wherein m is 1 to 6 and X is selected from the group consisting of Gly, His, Tyr, Trp, Val, Leu, Ser, Lys, Phe, Met, Ala, Glu, Ile, Thr, Asp, Asn, Gln, Arg, Cys, and Pro;

$X^{15}$ is a bond or an aspartate residue; and n is at least 2.

* * * * *

SEQUENCE LISTING

<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:synthesized
      sequence

<400> SEQUENCE: 1

Asp Tyr Lys Asp Asp Asp Asp Lys
  1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:synthesized
      sequence

<400> SEQUENCE: 2

Asp Asp Asp Lys
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:synthesized
      sequence

<400> SEQUENCE: 3

Asp Asp Asp Asp Lys
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:synthesized
      sequence
<221> NAME/KEY: ACT_SITE
<222> LOCATION: (6)
<223> OTHER INFORMATION: X is a non-acidic amino acid

<400> SEQUENCE: 4

Leu Val Pro Arg Gly Xaa
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:synthesized
      sequence
<221> NAME/KEY: ACT_SITE
<222> LOCATION: (5)
<223> OTHER INFORMATION: X is an amino acid except Proline or Arginine

<400> SEQUENCE: 5

Ile Glu Gly Arg Xaa
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:synthesized
      sequence
<221> NAME/KEY: ACT_SITE
<222> LOCATION: (5)
<223> OTHER INFORMATION: X is an amino acid except Proline or Arginine

<400> SEQUENCE: 6

Ile Asp Gly Arg Xaa
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:synthesized
      sequence
<221> NAME/KEY: ACT_SITE
<222> LOCATION: (5)
<223> OTHER INFORMATION: X is an amino acid except Proline or Arginine

<400> SEQUENCE: 7

Ala Glu Gly Arg Xaa
 1               5

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence:Primer

<400> SEQUENCE: 8
gaagaattca ccatggacta caaagaccat gacggtgatt ataaagatca tgat          54

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence:Primer

<400> SEQUENCE: 9
atcatgatct ttataatcac cgtcatggtc tttgtagtcc atggtgaatt cttc          54

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 10
gaagatatcg attacaagga tgacgatgac aagcttggg                           39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:Primer

```
<400> SEQUENCE: 11
cccaagcttg tcatcgtcat ccttgtaatc gatatcttc                                    39

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:synthesized
      sequence

<400> SEQUENCE: 12

Asp Tyr Lys Asp His Asp
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:synthesized
      sequence
<221> NAME/KEY: DNA_BIND
<222> LOCATION: (4)..(5)
<223> OTHER INFORMATION: X is any amino acid
<221> NAME/KEY: DNA_BIND
<222> LOCATION: (7)..(8)
<223> OTHER INFORMATION: X is any amino acid

<400> SEQUENCE: 13

Asp Tyr Lys Xaa Xaa Asp Xaa Xaa
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:synthesized
      sequence
<221> NAME/KEY: DNA_BIND
<222> LOCATION: (3)..(4)
<223> OTHER INFORMATION: X is any amino acid
<221> NAME/KEY: DNA_BIND
<222> LOCATION: (7)..(8)
<223> OTHER INFORMATION: X is any amino acid

<400> SEQUENCE: 14

Asp Tyr Xaa Xaa Asp Asp Xaa Xaa
 1               5
```